United States Patent
Coulter et al.

(10) Patent No.: US 9,255,068 B2
(45) Date of Patent: Feb. 9, 2016

(54) CRYSTALLINE SALTS OF (4S,4AS,5AR,12AS)-4-DIMETHYLAMINO-3,10,12,12A-TETRAHYDROXY-7-[METHOXY (METHYL)AMINO)-METHYL] ACID AMIDE AND METHODS OF USING THE SAME

(75) Inventors: Catherine Coulter, Ballymena (GB); Sean M. Johnston, Doylestown, PA (US); Farzaneh Seyedi, Mansfield, MA (US)

(73) Assignees: Warner Chilcott Company, LLC, Fajardo, PR (US); Paratek Pharmaceuticals, Inc., Boston, MA (US)

( * ) Notice: Subject to any disclaimer, the term of this patent is extended or adjusted under 35 U.S.C. 154(b) by 271 days.

(21) Appl. No.: 13/471,275

(22) Filed: May 14, 2012

(65) Prior Publication Data
US 2013/0012480 A1 Jan. 10, 2013

Related U.S. Application Data

(60) Provisional application No. 61/485,179, filed on May 12, 2011.

(51) Int. Cl.
- *A61K 31/65* (2006.01)
- *C07C 237/26* (2006.01)
- *C07C 309/04* (2006.01)
- *C07C 239/20* (2006.01)

(52) U.S. Cl.
CPC ............. *C07C 309/04* (2013.01); *C07C 239/20* (2013.01); *C07B 2200/07* (2013.01); *C07B 2200/13* (2013.01); *C07C 2103/46* (2013.01)

(58) Field of Classification Search
CPC .......................... C07C 237/26; C07B 2200/13
USPC ........................................... 552/203; 514/152
See application file for complete search history.

(56) References Cited

U.S. PATENT DOCUMENTS

| 2008/0312193 A1 | 12/2008 | Assefa et al. |
| 2010/0113399 A1 | 5/2010 | Cvetovich et al. |
| 2010/0305072 A1 | 12/2010 | Kim et al. |

FOREIGN PATENT DOCUMENTS

| WO | 2008/079339 A2 | 7/2008 |
| WO | 2008/079363 A2 | 7/2008 |

OTHER PUBLICATIONS

International Search Report and Written Opinion issued in PCT/US2012/037838, filed May 14, 2012 (8 Pages).
Extended European Search Report issued in Corresponding European Application No. 12782600.6, dated Oct. 13, 2014 (6 Pages).

*Primary Examiner* — Barbara P Badio
(74) *Attorney, Agent, or Firm* — Fitzpatrick, Cella, Harper & Scinto

(57) ABSTRACT

A crystalline mono hydrochloride salt of (4S,4aS,5aR,12aS)-4-dimethylamino-3,10,12,12a-tetrahydroxy-7-[(methoxy (methyl)amino)-methyl]-1,11-dioxo-1,4,4a,5,5a,6,11,12a-octahydro-naphthacene-2-carboxylic acid amide is disclosed having improved stability. In addition, a crystalline mono mesylate salt and crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide are also disclosed having improved stability. A pharmaceutical composition containing the crystalline salts and methods of treating inflammatory skin disorders and bacterial infections comprising administering the crystalline salts are also disclosed.

72 Claims, 11 Drawing Sheets

CRYSTALLINE SALTS OF (4S,4AS,5AR,12AS)-4-DIMETHYLAMINO-3,10,12,12A-TETRAHYDROXY-7-[METHOXY(METHYL)AMINO)-METHYL] ACID AMIDE AND METHODS OF USING THE SAME

CROSS-REFERENCE TO RELATED APPLICATIONS

This application claims the benefit of priority from U.S. Provisional Application No. 61/485,179, filed May 12, 2011, the content of which is incorporated by reference herein in its entirety.

FIELD OF THE INVENTION

The instant disclosure relates to crystalline mono hydrochloride, mono mesylate, and mono sulfate salts of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, and methods of using the same. More specifically, the disclosure relates to crystalline mono hydrochloride, mono mesylate, and mono sulfate salts of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide having improved stability over tetracycline compounds known in the art. In addition, the instant disclosure relates to pharmaceutical compositions comprising the crystalline mono hydrochloride, mono mesylate, or mono sulfate salts of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, and methods of treating acne, rosacea or gram positive bacterial infections using the crystalline mono hydrochloride, mono mesylate, or mono sulfate salts of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide.

BACKGROUND OF THE INVENTION

Tetracyclines are known "broad spectrum" antibiotics and have become widely used for therapeutic purposes. Tetracyclines have been found to be highly effective pharmacologically against rickettsiae; a number of gram-positive and gram-negative bacteria; and the agents responsible for lymphogranuloma venereum, inclusion conjunctivitis, and psittacosis. The first use of tetracycline antibiotics dates as far back as 1948. Examples of pharmaceutically active tetracycline and tetracycline analogue compositions may be found in U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. Tetracyclines may also be used to treat inflammatory skin disorders, including dermatitis, psoriasis, pyoderma gangrenosum, acne and rosacea.

Acne vulgaris, also referred to as acne, is both an inflammatory skin disorder and a bacterial infection. It is a disorder resulting from hormones affecting the sebaceous glands, which leads to plugged pores and outbreaks of lesions, or pimples. Acne is the most common skin disease in the United States, affecting nearly 17 million people. Severe acne can lead to disfiguration, and permanent scarring.

Acne is described as a disorder of the pilosebaceous units (PSUs). Found over most of the body, PSUs consist of sebaceous glands, which make an oily substance that normally empties onto the skin surface through the opening of the follicle, also called a pore. When the pore is plugged, the mixture of oil and cells allows bacteria that normally live on the skin to grow in the plugged follicles, which produce chemicals and enzymes and attract white blood cells that cause inflammation. The plugged follicle breaks down, the sebum, shed skin cells and bacteria disseminate into the nearby tissues, leading to lesions or pimples.

Acne is commonly treated with systemic antibiotics, including tetracyclines, to reduce the growth of bacteria. Efficacy is thought to be due to an effect on *Propionibacterium acnes* (*P. acnes*) as well as the intrinsic anti-inflammatory properties of these antibiotics. *Propionibacterium acnes* is a relatively slow growing, typically aerotolerant anaerobic gram positive bacterium (rod) that is linked to acne. Tetracyclines are known to be effective in killing *P. acnes* and other bacteria and have been used to treat acne because of their antibacterial and anti-inflammatory properties.

Rosacea is a skin disorder characterized by facial redness, mainly affecting individuals of north western European descent. Early symptoms of rosacea include redness on the chin, nose, skin or forehead; small visible blood vessels on the face; bumps or pimples on the face; and watery and irritated eyes. Although the causes of rosacea are poorly understood, systemic antibiotics, such as tetracyclines, are commonly prescribed for the treatment of rosacea, due to both their anti-inflammatory and antibacterial properties.

After the widespread use of tetracyclines for both major and minor illnesses and diseases led to resistance to these antibiotics, substituted tetracycline compounds were developed to treat bacterial infections, inflammation, neoplasms, and other conditions. The term "tetracycline compound" includes many compounds with a similar ring structure to tetracycline. Examples of these tetracycline compounds include: chlortetracycline, doxycycline, minocycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline. For example, substituted tetracycline compounds have been disclosed in WO 2008/079339 and WO 2008/079363.

One substituted tetracycline compound is (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, described in U.S. Patent Application Publication Nos. 2008/0312193 and 2010/0305072. The free base of this compound has proven unstable for use as an active pharmaceutical ingredient. In addition, while those skilled in the art have attempted to synthesize a salt of this compound previously, only amorphous salts have been produced and these amorphous salts have shown only minimal improved stability over the free base. Accordingly, there exists a need in the art for improved stability of this substituted tetracycline compound.

The present invention is directed to the novel crystalline mono hydrochloride, mono mesylate, and mono sulfate salts of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, which exhibit superior stability over the free base and previously known salts thereof. This is a significant advancement in the state of the art.

SUMMARY OF THE INVENTION

The present invention is directed to a crystalline salt of (4S,4aS,5aR,12aS)-4-dimethylamino-3,10,12,12a-tetrahydroxy-7-[(methoxy(methyl)amino)-methyl]-1,11-dioxo-1,4, 4a,5,5a,6,11,12a-octahydro-naphthacene-2-carboxylic acid amide, wherein the salt is selected from a group consisting of mono hydrochloride, mono mesylate and mono sulfate. In a certain embodiment, the crystalline salt is substantially pure. One embodiment is directed to the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide. In a certain embodiment, the crystalline mono hydrochloride salt has an X-ray powder diffraction (XRPD) pattern substantially as illustrated in FIG. 1 after synthesis of the crystalline salt, and, in a preferred embodiment, has characteristic peaks in the XRPD pattern at diffraction angle 2-theta degrees appearing at least at about 13.4, about 20.5 and about 23.3. In further embodiments, the crystalline mono hydrochloride salt has a differential scanning calorimetry (DSC) curve substantially as illustrated in FIG. 2 after synthesis, and a thermo-gravimetric analysis (TGA) curve substantially as illustrated in FIG. 3 after synthesis. In another embodiment, the crystalline mono hydrochloride salt has a β-isomer content at 0 days of about 0.1 percent peak area (hereinafter referred to as "% peak area") to about 7.0% peak area, as measured by High Performance Liquid Chromatography (HPLC).

Other embodiments of the invention are directed to a crystalline mono mesylate salt and a crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide. In a certain embodiment, the crystalline mono mesylate salt has an XRPD pattern substantially as illustrated in FIG. 4 after synthesis of the crystalline salt, and, in a preferred embodiment, has characteristic peaks in the XRPD pattern at diffraction angle 2-theta degrees appearing at least at about 9, about 15 and about 23.8. In further embodiments, the crystalline mono mesylate salt has a DSC curve substantially as illustrated in FIG. 5 after synthesis, and a TGA curve substantially as illustrated in FIG. 6 after synthesis.

In a certain embodiment, the crystalline mono sulfate salt has an XRPD pattern substantially as illustrated in FIG. 7 after synthesis of the crystalline salt, and, in a preferred embodiment, has characteristic peaks in the XRPD pattern at diffraction angle 2-theta degrees appearing at least at about 15, about 17.8 and about 23.5. In further embodiments, the crystalline mono sulfate salt has a DSC curve substantially as illustrated in FIG. 8 after synthesis, and a TGA curve substantially as illustrated in FIG. 9 after synthesis.

In preferred embodiments, the crystalline mono mesylate salt has a β-isomer content at 0 days of about 2.0% peak area to about 10.0% peak area, as measured by HPLC, and the crystalline mono sulfate salt have a β-isomer content at 0 days of about 3.0% peak area to about 26.0% peak area, as measured by HPLC.

The present invention is further directed to a pharmaceutical composition comprising a crystalline mono hydrochloride salt, crystalline mono mesylate salt or crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide and a pharmaceutically acceptable excipient. In one embodiment, the pharmaceutical composition is used for treating acne. In another embodiment, the pharmaceutical composition is used for treating rosacea. In yet another embodiment, the pharmaceutical composition is used for treating a gram positive bacterial infection, wherein the gram positive bacteria is selected from the group consisting of *Propionibacterium acnes, Staphylococcus aureus, Streptococcus pneumonia, Streptococcus pyogenes*, and *Clostridium difficile*.

The present invention is also directed to a method of treating acne comprising administering to a subject a therapeutically effective amount of a crystalline mono hydrochloride salt, crystalline mono mesylate salt, or crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide.

The present invention is also directed to a method of treating rosacea comprising administering to a subject a therapeutically effective amount of a crystalline mono hydrochloride salt, crystalline mono mesylate salt, or crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide.

The present invention is also directed to a method of treating a gram positive bacterial infection, wherein the gram positive bacteria is selected from the group consisting of *Propionibacterium acnes, Staphylococcus aureus, Streptococcus pneumonia, Streptococcus pyogenes*, and *Clostridium difficile*, comprising administering to a subject a therapeutically effective amount of a crystalline mono hydrochloride salt, crystalline mono mesylate salt, or crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide.

DETAILED DESCRIPTION OF THE INVENTION

Crystalline Salts

Figure 1:
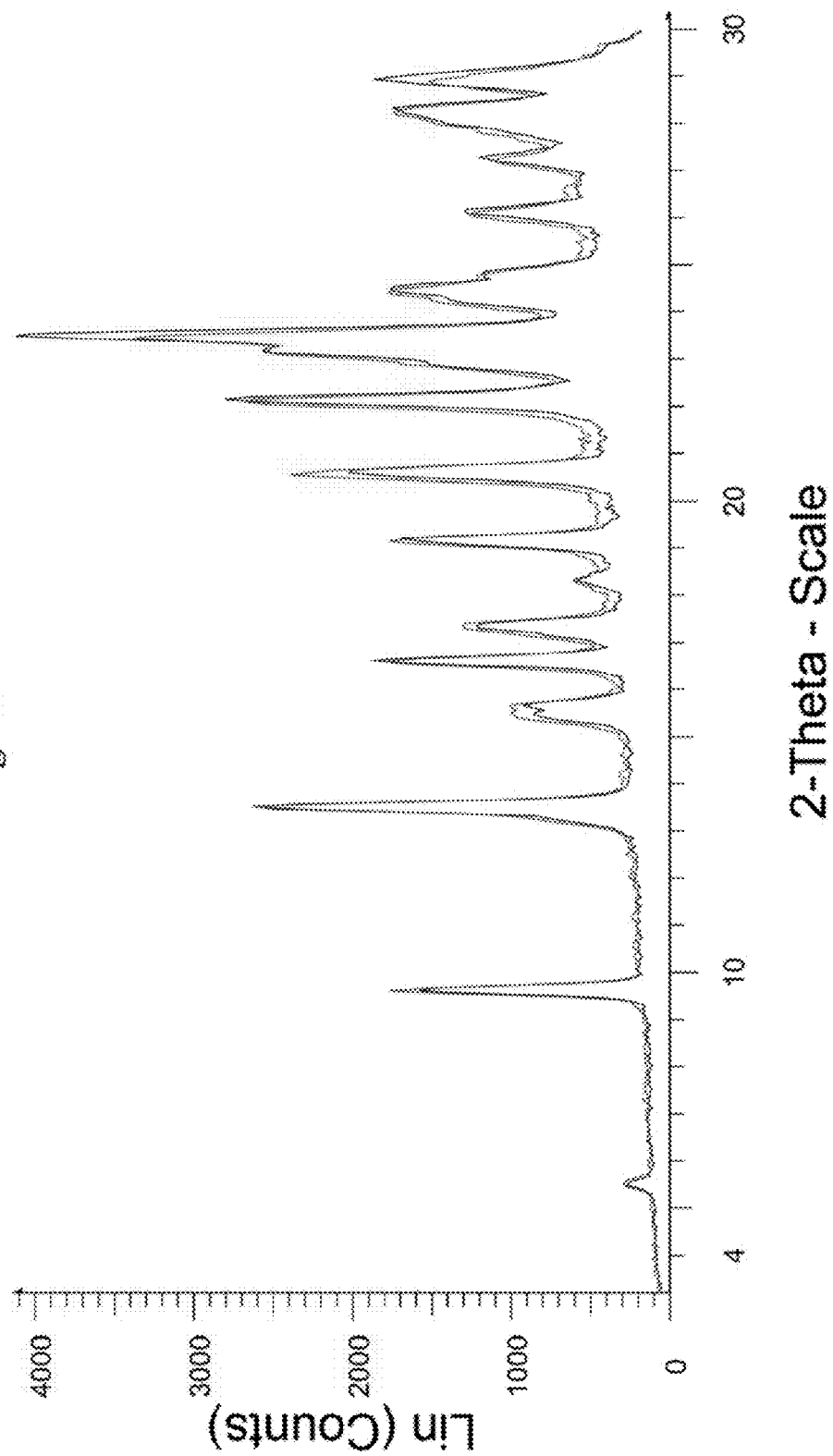
FIG. 1 shows X-ray powder diffraction (XRPD) analysis of crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide after synthesis and after storage for 7 days at 40° C. and 75% relative humidity (RH).

Novel crystalline salts of (4S,4aS,5aR,12aS)-4-dimethylamino-3,10,12,12a-tetrahydroxy-7-[(methoxy(methyl) amino)-methyl]-1,11-dioxo-1,4,4a,5,5a,6,11,12a-octahydro-naphthacene-2-carboxylic acid amide are disclosed herein. After much experimentation and discovery, the inventors determined the stable and preferred salt forms of (4S,4aS, 5aR,12aS)-4-dimethylamino-3,10,12,12a-tetrahydroxy-7-[(methoxy(methyl)amino)-methyl]-1,11-dioxo-1,4,4a,5,5a, 6,11,12a-octahydro-naphthacene-2-carboxylic acid amide, which may be used as a pharmaceutical active ingredient in a pharmaceutical composition. The present disclosure teaches how to make these novel crystalline salts and the superior benefits of them over the free base of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide and previously known amorphous salts thereof.

Thus, one embodiment of the present invention is a crystalline salt of (4S,4aS,5aR,12aS)-4-dimethylamino-3,10,12, 12a-tetrahydroxy-7-[(methoxy(methyl)amino)-methyl]-1, 11-dioxo-1,4,4a,5,5a,6,11,12a-octahydro-naphthacene-2-carboxylic acid amide, wherein the salt is selected from a group consisting of mono hydrochloride, mono mesylate and mono sulfate.

In a preferred embodiment, the crystalline salt is substantially pure. A substantially pure crystalline salt contains less than about 10% peak area and, preferably, less than about 4% peak area, total impurity content, as measured by HPLC. In a more preferred embodiment, the crystalline salt is substantially free of an amorphous salt. Preferably, less than about 8% peak area of amorphous salt is present, more preferably, less than about 5% peak area of amorphous salt is present, and still more preferably, less than about 3% peak area of amorphous salt is present.

As used herein in reference to the percent peak area of impurity content, the term "about" generally means within 10 percent, e.g., within 5 percent of a given value or range.

The term "crystalline" as used herein refers to compounds in a solid state having a periodic and repeating three-dimensional internal arrangement of atoms, ions or molecules characteristic of crystals. The term crystalline does not necessarily mean that the compound exists as crystals, but that it has this crystal-like internal structural arrangement. The term "amorphous" as used herein refers to compounds lacking a crystalline structure: no repeating pattern, only short range order, extensively disordered.

The crystalline salts of (4S,4aS,5aR,12aS)-4-dimethylamino-3,10,12,12a-tetrahydroxy-7-[(methoxy(methyl) amino)-methyl]-1,11-dioxo-1,4,4a,5,5a,6,11,12a-octahydro-naphthacene-2-carboxylic acid amide may be used to treat, prevent, or otherwise ameliorate bacterial, viral, parasitic, and fungal infections; cancer (e.g., prostate, breast, colon, lung melanoma and lymph cancers) and other disorders characterized by unwanted cellular proliferation; arthritis; osteoporosis; diabetes; stroke; acute myocardial infarction; aortic aneurysm; neurodegenerative diseases and other conditions for which tetracycline compounds have been found to be active (see, for example, U.S. Pat. Nos. 5,789,395; 5,834,450; 6,277,061; and 5,532,227, each of which is expressly incorporated herein by reference). In addition, the salts of the invention can be used to prevent or control important mammalian and veterinary diseases such as rickettsial infections, sexually transmitted infections, respiratory tract infections, bacterial infections, ophthalmic infections, anthrax; may serve as therapy in acute intestinal amebiasis, acne, and lyme disease; and may be used for prophylaxis of malaria and the like. Preferably, the crystalline salts of the present invention may be used to treat bacterial infections and inflammatory skin disorders, which include, without limitation, eczema, dermatitis, psoriasis, pyoderma gangrenosum, acne and rosacea. In one embodiment, the crystalline salts of the present invention may be used to treat acne and/or rosacea. For example, the crystalline salts of the present invention may be used to treat acne. Nonlimiting examples of bacterial infections that can be treated by the salts of the invention include infections with gram positive organisms *Propionibacterium acnes, Staphylococcus aureus, Streptococcus pneumonia, Streptococcus pyogenes*, or *Clostridium difficile*.

A certain embodiment is the crystalline mono hydrochloride salt of (4S,4aS,5aR,12aS)-4-dimethylamino-3,10,12, 12a-tetrahydroxy-7-[(methoxy(methyl)amino)-methyl]-1, 11-dioxo-1,4,4a,5,5a,6,11,12a-octahydro-naphthacene-2-carboxylic acid amide.

The term "mono hydrochloride salt" as used herein refers to an ionic compound that results from the neutralization reaction of an acid and a base. The ionic compound (herein, HCl) is composed of a cation and an anion so that the compound is neutral.

General methods for analyzing crystalline salts include crystal analysis by X-ray powder diffraction (XRPD), differential scanning calorimetry (DSC) and thermo-gravimetric analysis (TGA).

XRPD analysis as disclosed herein was collected on a Bruker AXS C2 GADDS diffractometer using Cu Kα radiation (40 kV, 40 mA), automated XYZ stage, laser video microscope for auto-sample positioning and a HiStar 2-dimensional area detector. X-ray optics consisted of a single Gobel multilayer mirror coupled with a pinhole collimator of 0.3 mm. The software used for data collection was GADDS for WNT 4.1.16 and the data was analyzed and presented using Diffrac Plus EVA v 9.0.0.2 or v 13.0.0.2. Samples were analyzed under ambient conditions as flat plate specimens using powder as received. Approximately 1-2 mg of the sample was lightly pressed on a glass slide to obtain a flat surface. Samples analyzed under non-ambient conditions were mounted on a silicon wafer with a heat conducting compound. The sample was then heated to the appropriate temperature at approximately 20° C. min$^{-1}$ and subsequently held isothermally for approximately 1 minute before data collection was initiated.

In certain embodiments, the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide has an XRPD pattern substantially as illustrated in FIG. 1 after synthesis of the crystalline salt.

The term "XRPD pattern" as used herein refers to the graphical representation of the data collected by XRPD analysis. XRPD analysis is a technique used to characterize the crystallographic structure, size, and preferred orientation in polycrystalline or powdered solid samples. This diffraction is also used to characterize heterogeneous solid mixtures to determine the percent of crystalline compounds present and can provide structural information on unknown materials.

The terms "substantially" and "about" as used herein in reference to an XPRD pattern refer to the XPRD pattern wherein a listed peak(s) appears within 0.2 degrees 2-theta, including within 0.1 degrees 2-theta of a given 2-theta value.

In a preferred embodiment, the crystalline mono hydrochloride salt has characteristic peaks at diffraction angle 2-theta degrees appearing at least at about 13.4, about 20.5 and about 23.3, as measured by XRPD. In a more preferred embodiment, the crystalline mono hydrochloride salt has characteristic peaks at diffraction angle 2-theta degrees appearing at least at about 9.5, about 13.4, about 15.5, about 20.5 and about 23.3, as measured by XRPD, and still more preferable, the crystalline mono hydrochloride salt has characteristic peaks at diffraction angle 2-theta degrees appearing at least at about 9.5, about 13.4, about 15.5, about 16.6, about 19.2, about 20.5, about 22.2, and about 23.3.

The term "characteristic peak" as used herein refers to a peak in the XRPD pattern having an intensity at least 20%, more preferably 40% greater than the baseline noise.

TGA and DSC analysis are used to measure thermal behavior and can be used to distinguish between polymorphs. One polymorphic form may exhibit thermal behavior different from that of the amorphous material or another polymorphic form.

DSC analysis as disclosed herein was collected on a TA Instruments Q2000 equipped with a 50 position auto-sampler. The instrument was calibrated for energy and temperature using certified indium. The calibration for thermal capacity was carried out using sapphire. Typically, 0.5-3.0 mg of each sample, in a pin-holed aluminum pan, was heated at 10° C.min$^{-1}$ from 25° C. to 250° C. A nitrogen purge at 50 ml.min$^{-1}$ was maintained over the sample. The instrument control software used was Advantage for Q Series v2.8.0.392 and Thermal Advantage v4.8.3 and the data was analyzed using Universal Analysis v4.4A.

DSC is a thermoanalytical technique in which the difference in the amount of heat required to increase the temperature of a sample and reference is measured as a function of temperature. DSC can be used to measure a number of characteristic properties of a sample, allowing observation of crystallization events. Specifically, with DSC, it is possible to observe small energy changes that occur as matter transitions from a solid to a liquid crystal and from a liquid crystal to an isotropic liquid. The presence of events in the DSC curve can be used to assess the compound's stability, as well as the presence of solvates or hydrates.

TGA is used to determine changes in weight in relation to change in temperature, which may reveal degradation of the compound and the presence of solvates or hydrates. TGA analysis as disclosed herein was collected on a TA Instruments Q500 TGA equipped with a 16 position auto-sampler. The instrument was temperature calibrated using certified Alumel and Nickel. Typically, 5-30 mg of each sample was loaded onto a pre-weighed platinum crucible and aluminum DSC pan and was heated at 10° C. min$^{-1}$ from ambient temperature to 300° C. A nitrogen purge at 60 ml.min$^{-1}$ was maintained over the sample. The instrument control and data analysis software used was Advantage for Q Series v2.8.0.392 and Thermal Advantage v4.8.3 and the data was analyzed using Universal Analysis v4.4A.

Figure 2:
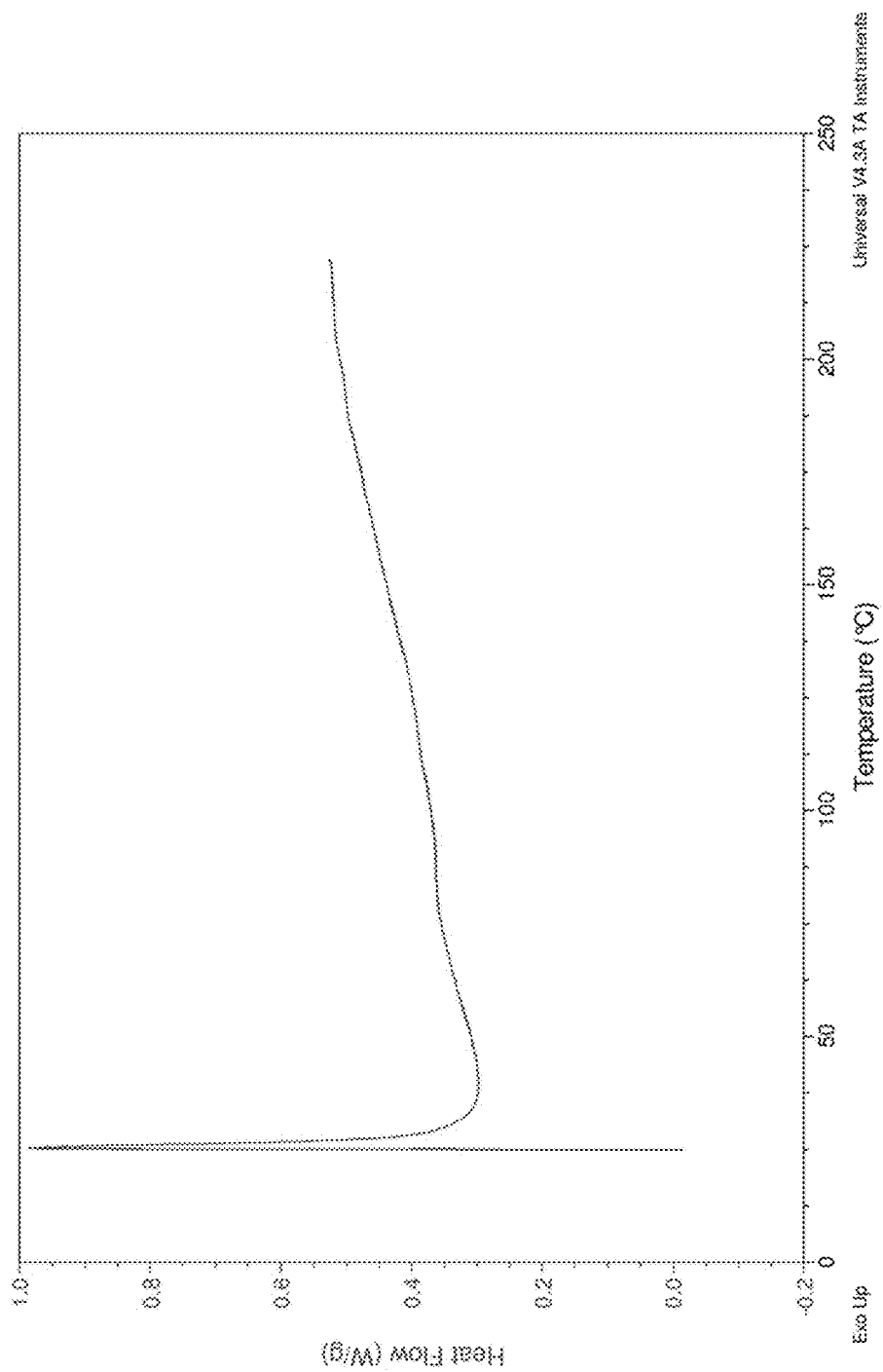
FIG. 2 is a differential scanning calorimetry (DSC) curve of crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide after synthesis.

In a certain embodiment, the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide exhibits a DSC curve substantially as illustrated in FIG. 2. Preferably, the crystalline mono hydrochloride salt analyzed by DSC exhibits no events up to degradation of the crystalline salt.

The term "events" as used herein refers to a change in the sample associated with absorption (endothermic) or evolution (exothermic) of heat causing a change in differential heat flow which is recorded as a peak in the thermogram. Such changes in the sample include decomposition, degradation, and change of form or morphology, solvate or hydrate. The absence of any events indicates that the compound is stable and is in a low energy form.

The term "substantially," as used herein in reference to DSC curve means the DSC curve demonstrating a peak(s) within 1° C., including within 0.5° C. of a given temperature.

Figure 3:
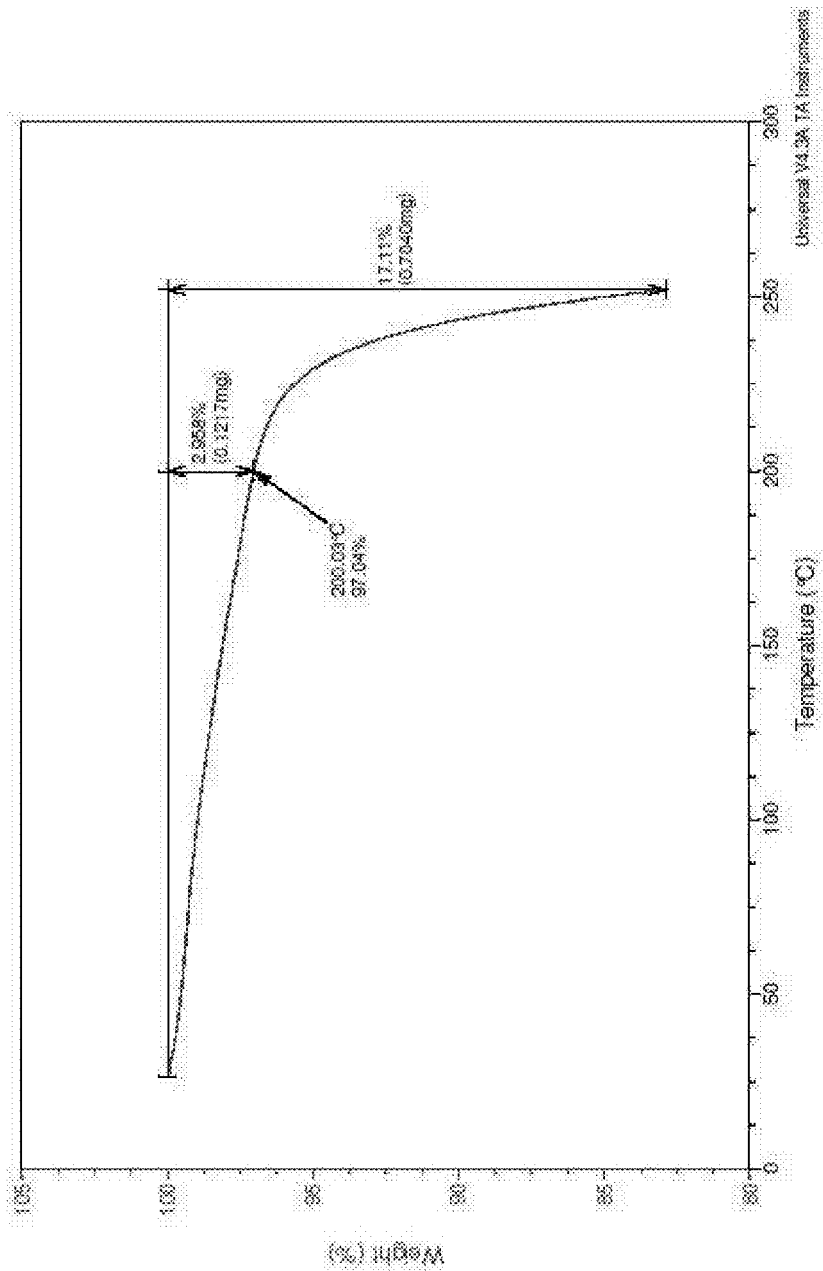
FIG. 3 is a thermo-gravimetric analysis (TGA) curve of crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide after synthesis.

In a certain embodiment, the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide exhibits a TGA curve substantially as illustrated in FIG. 3. Preferably, the crystalline mono hydrochloride salt analyzed by TGA exhibits a weight loss of about 1% to about 5% from about 30° C. to about 200° C. and a weight loss of about 12% to about 16% from about 200° C. to about 250° C. and, more preferably, a weight loss of about 3% from about 30° C. to about 200° C. and a weight loss of about 14% to about 15% from about 200° C. to about 250° C.

The term "substantially," as used herein in reference to the TGA curve means the curve demonstrating a percent weight loss within 1%, including within 0.5% of a given value in relation to temperature change.

In certain embodiments, the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide is stable for at least 4 months, and more preferably for at least 6 months.

The term "stable" and "stability" as used herein refers to both the physical form and the chemical purity of the salt. "The salt" as used herein refers to the disclosed crystalline mono hydrochloride, mono mesylate and mono sulfate salts of the present invention.

One measure of the stability of the physical form of the salt is hygroscopicity, which is the propensity of a substance to absorb or adsorb water molecules from the surrounding environment. Whenever moisture can promote degradation, the salt is stable if it is non-hygroscopic or mildly hygroscopic above 70% relative humidity (RH). In preferred embodiments, the salt is non-hygroscopic or mildly hygroscopic above 80% RH, and in more preferred embodiments, the salt is non-hygroscopic or mildly hygroscopic to 90% RH. "Non-hygroscopic or mildly hygroscopic" as used herein refers to a compound at about 40° C. and at an RH of about 75%, existing over about 80% w/w in solid crystalline form, preferably over about 90% w/w in solid crystalline form, that absorbs less than 10% w/w water, and preferably, less than 5% w/w water in 8 hours or less. Hygroscopicity (hygroscopic degree) is calculated based on increase in weight in a compound at comparative points of measurement. Another measure of physical stability is the crystal form of the salt, which may be measured by XPRD.

One measure of chemical purity is defined by the β-isomer content of the salt. Many tetracyclines are optically active and contain one or more asymmetric centers. The process by which the asymmetry of such a center is altered to form the opposite stereochemistry is referred to as epimerization. Tetracyclines undergo reversible epimerization to the less active epi-tetracycline. The rate at which epimerization occurs is dependent on many factors, such as pH, temperature, counter ion, and humidity. The naturally occurring epimer is typically referred to as α, or the active epimer. The other epimer, known as β, may or may not possess biological activity.

(4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide has an epimeric center at $C_4$. The α and β epimers of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide are separable and quantifiable by reversed phase HPLC (High Performance Liquid Chromatography) with ultraviolet detector (HPLC-UV) analysis, and measured as percent area under the curve, also referred to as percent peak area. Although the epimer of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide is believed to be non-toxic, under certain conditions it may lack the anti-bacterial efficacy of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide and, therefore, is considered an undesirable degradation product.

The lower the β-isomer content, the higher the chemical purity of the salt. The β-isomer content is measured after synthesis of the salt and compared with the measured β-isomer content after storage for a designated period of time. Where the β-isomer content does not significantly increase after storage, there has been no negative effect of storage on the chemical purity of the salt and the salt is stable for that designated period of time. Since moisture uptake by the tetracycline may be a contributing factor to epimerization, a salt form of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide that is not significantly hygroscopic may provide an innate resistance to epimerization caused by humidity.

Another measure of chemical purity is defined by the content of other related impurities, by-products or degradation products of the salt, which represents the morphology of the compound. The lower the content of total impurities as measured by HPLC, generally, by HPLC-UV, the higher the chemical purity of the salt. The total impurity content is measured after synthesis of the salt and compared with the measured total impurity content after storage for a designated period of time. Where the total impurity content does not significantly increase after storage, there has been no negative effect of storage on the chemical purity of the salt and the salt is stable for that designated period of time.

In certain embodiments, at 0 days, the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide has a total impurity content of less than about 8% and, preferably, less than about 4%. In another embodiment, the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide has a total impurity content after storage for about 6 months at about 40° C. and about 75% RH of less than about 10% and, preferably, less than about 6%. In a certain embodiment, the salt has a total impurity content after storage for about 6 months at about 40° C. and about 75% RH not more than about 80% peak area greater than the total impurity content at about 0 days, and preferably, not more than about 50% peak area greater than the total impurity content at about 0 days.

In a certain embodiment of the present invention, the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide is stable and has a β-isomer content after storage for about 75 days at about 40° C. and about 75% RH not more than about 20% peak area greater than the β-isomer content at about 0 days. In a preferred embodiment, the salt has a β-isomer content after storage for about 75 days at about 40° C. and about 75% RH not more than about 10% peak area greater than the β-isomer content at about 0 days; in a more preferred embodiment, the β-isomer content after storage for about 75 days at about 40° C. and about 75% RH is not more than about 1% peak area greater than the β-isomer content at about 0 days; and in a further preferred embodiment, the β-isomer content after storage for about 75 days at about 40° C. and about 75% RH is about equal to the β-isomer content at about 0 days. "After synthesis" as used herein refers to less than about one day from the time of confirmation of synthesis, also referred to as "0 days."

In a certain embodiment, the β-isomer content of the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide at 0 days is about 0.1% to about 7.0% peak area, preferably about 1.0% to about 6.0% peak area, more preferably about 2.0% to about 4.0% peak area, and most preferably about 3.0% to about 4.0% peak area. In a certain embodiment, the β-isomer content of the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide after storage for at least 3 months is about 2.0% to about 8.0% peak area, and more preferably about 3.0% to about 4.0% peak area. In other embodiments, the β-isomer content after storage for at least 6 months is about 0.1% to about 10.0% peak area, and more preferably about 2.0% to about 8.0% peak area. In a certain embodiment, the β-isomer content of the crystalline mono hydrochloride salt of (4S,4aS,5aR,12aS)-4-dimethylamino-3,10,12,12a-tetrahydroxy-7-

[(methoxy(methyl)amino)-methyl]-1,11-dioxo-1,4,4a,5,5a, 6,11,12a-octahydro-naphthacene-2-carboxylic acid amide at 0 days is less than about 6.0% peak area and after storage for about 75 days at ambient conditions is less than about 6.0% peak area. Preferably, the β-isomer content at 0 days is less than about 4.5% peak area and after storage for about 75 days at ambient conditions is less than about 4.5% peak area, and in a still further embodiment, the β-isomer content at 0 days is about 3.8% peak area and after storage for about 75 days at ambient conditions is about 3.8% peak area.

Ambient conditions, as used herein, means a temperature of about 20° C. to about 25° C. and an RH of about 40%.

Another embodiment of the present invention is the crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide.

The term "mono mesylate salt" as used herein refers to an ionic compound that results from the neutralization reaction of an acid and a base. The compound is composed of a cation and an anion (herein, $CH_3SO_2^-$) so that the compound is neutral.

Figure 4:
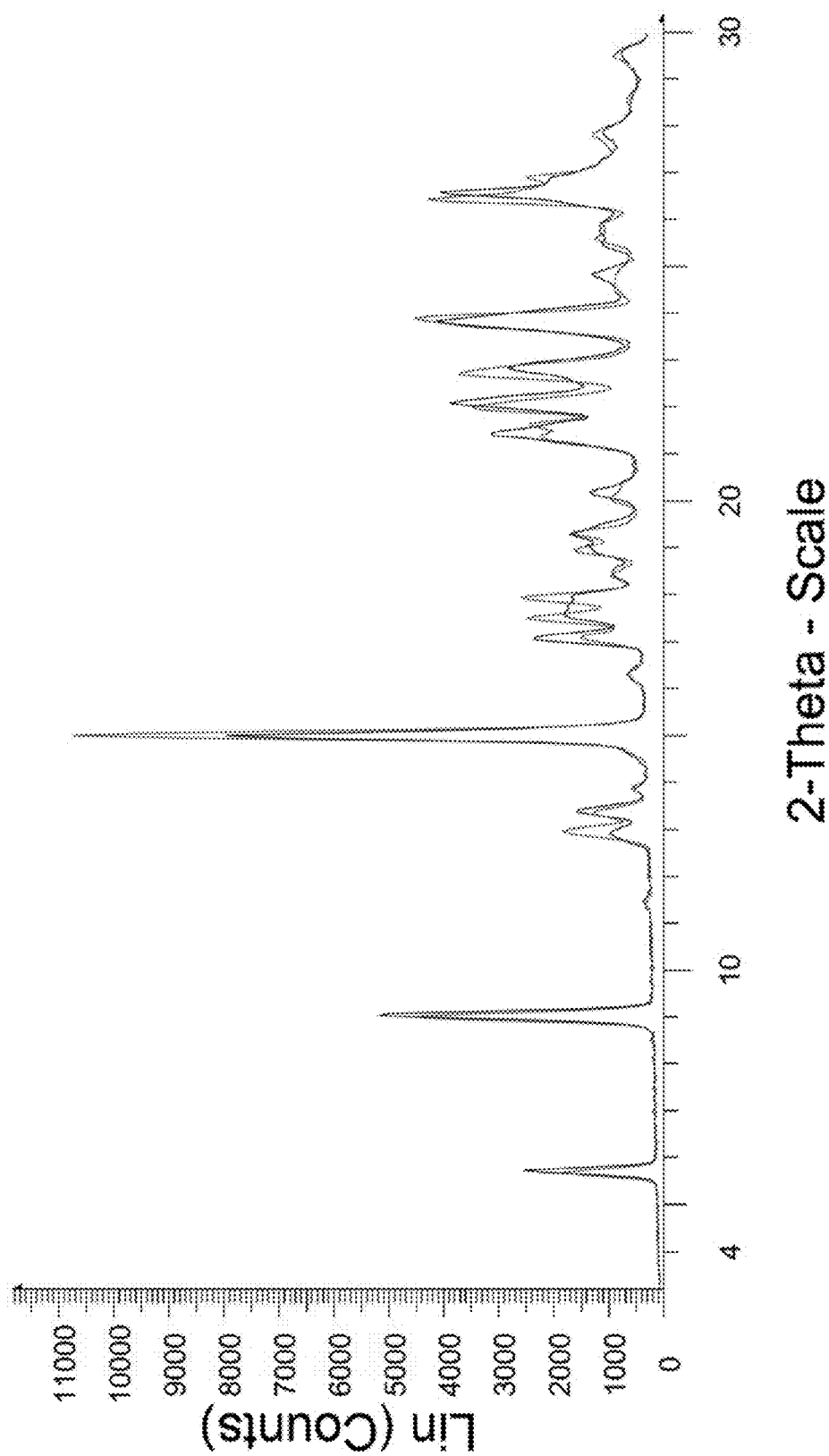
FIG. 4 shows XRPD analysis of crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide after synthesis and after storage for 7 days at 40° C. and 75% RH.

In certain embodiments, the crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide has an XRPD pattern substantially as illustrated in FIG. 4 after synthesis of the crystalline salt.

In a preferred embodiment, the crystalline mono mesylate salt has characteristic peaks at least appearing at diffraction angle 2-theta degrees appearing at about 9, about 15 and about 23.8, as measured by XRPD. In a more preferred embodiment, the crystalline mono mesylate salt has characteristic peaks at diffraction angle 2-theta degrees appearing at least at about 9, about 15, about 22.7 and about 23.8, as measured by XRPD, and still more preferable, the crystalline mono mesylate salt has characteristic peaks at diffraction angle 2-theta degrees appearing at least at about 9, about 15, about 22, about 22.7 and about 23.8.

Figure 5:
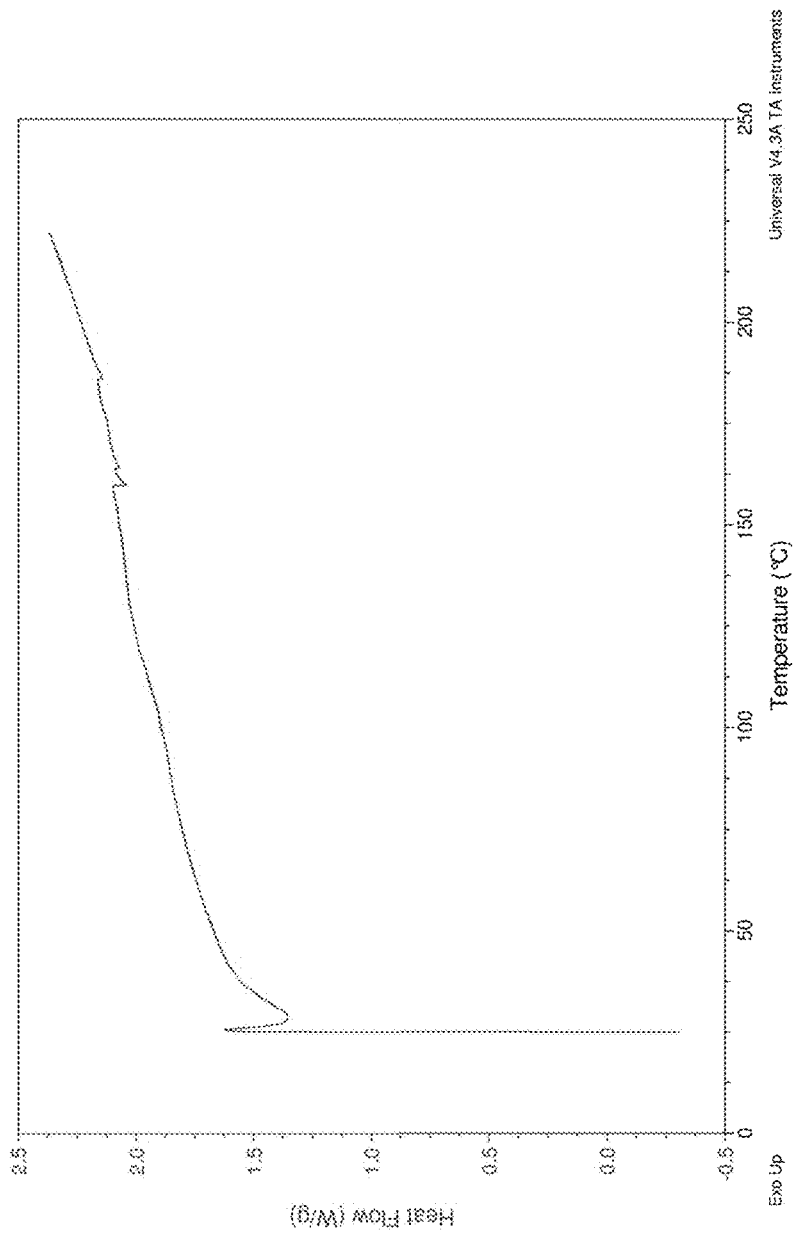
FIG. 5 is a DSC curve of crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide after synthesis.

In a certain embodiment, the crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide exhibits a DSC curve substantially as illustrated in FIG. 5. Preferably, the crystalline mono mesylate salt analyzed by DSC exhibits no events up to degradation of the crystalline salt.

Figure 6:
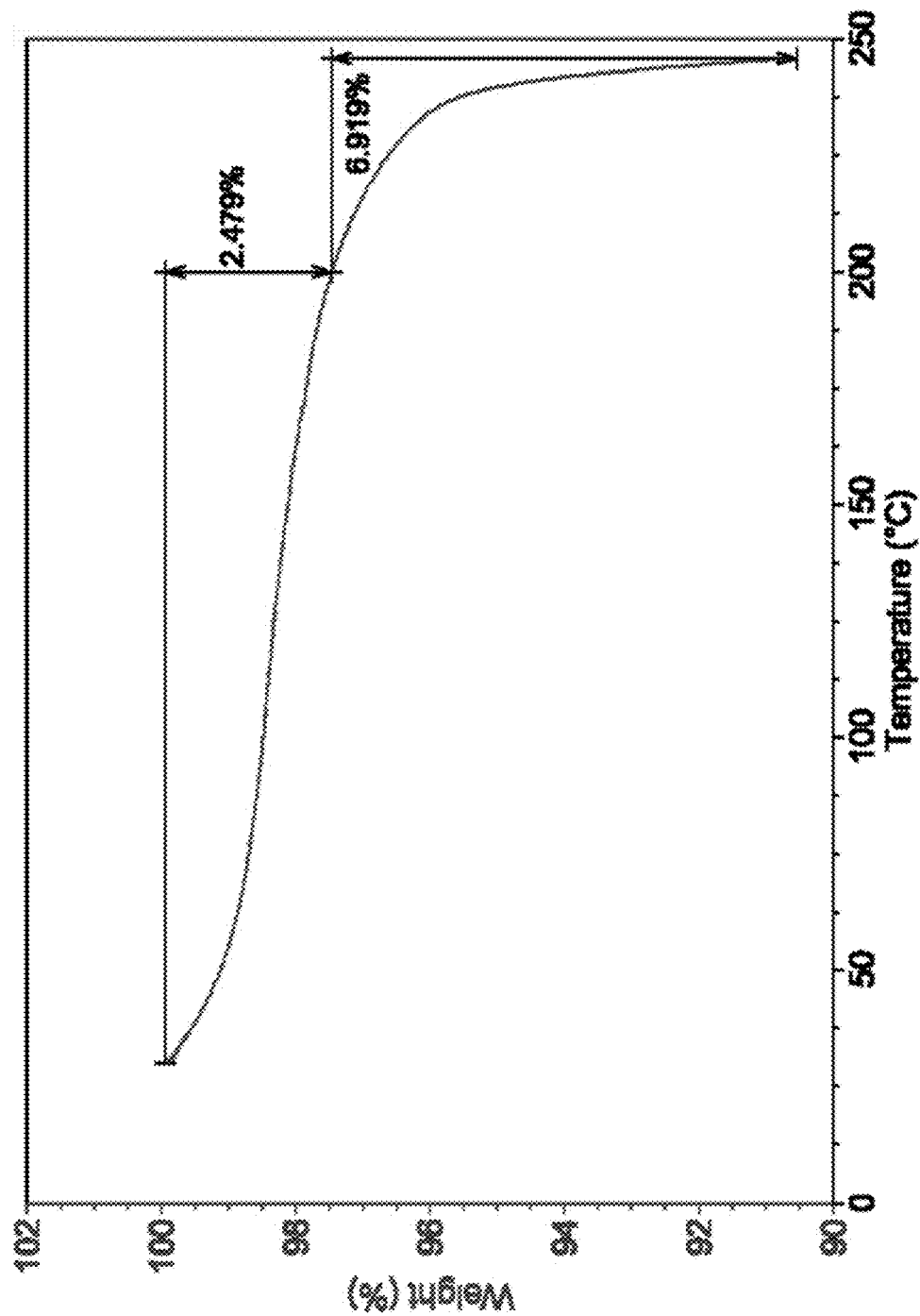
FIG. 6 is a TGA of crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4, 4a,5,5a,6,11,12a-octahydro-naphthacene-2-carboxylic acid amide after synthesis.

In a certain embodiment, the crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide exhibits a TGA curve substantially as illustrated in FIG. 6. Preferably, the crystalline mono mesylate salt analyzed by TGA exhibits a weight loss of about 1% to about 4% from about 30° C. to about 200° C. and a weight loss of about 3% to about 10% from about 200° C. to about 250° C. and, more preferably, a weight loss of about 2% to about 3% from about 30° C. to about 200° C. and a weight loss of about 6% to about 7% from about 200° C. to about 250° C.

In a certain embodiment of the present invention, the crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide is stable and has a β-isomer content after storage for about 75 days at about 40° C. and about 75% RH not more than about 20% peak area greater than the β-isomer content at about 0 days. In a preferred embodiment, the salt has a β-isomer content after storage for about 75 days at about 40° C. and about 75% RH not more than about 10% peak area greater than the β-isomer content at about 0 days; in a more preferred embodiment, the β-isomer content after storage for about 75 days at about 40° C. and about 75% RH is not more than about 1% peak area greater than the β-isomer content at about 0 days; and in a further preferred embodiment, the β-isomer content after storage for about 75 days at about 40° C. and about 75% RH is about equal to the β-isomer content at about 0 days.

In a certain embodiment, the β-isomer content of the crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide at 0 days is about 2.0% to about 10.0% peak area, preferably about 2.0% to about 6.0% peak area, and more preferably about 2.0% to about 3.0% peak area.

Another embodiment of the present invention is a crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide.

The term "mono sulfate salt" as used herein refers to an ionic compound that results from the neutralization reaction of an acid and a base. The compound is composed of a cation and an anion (herein, $SO_4^{2-}$) so that the compound is neutral.

Figure 7:
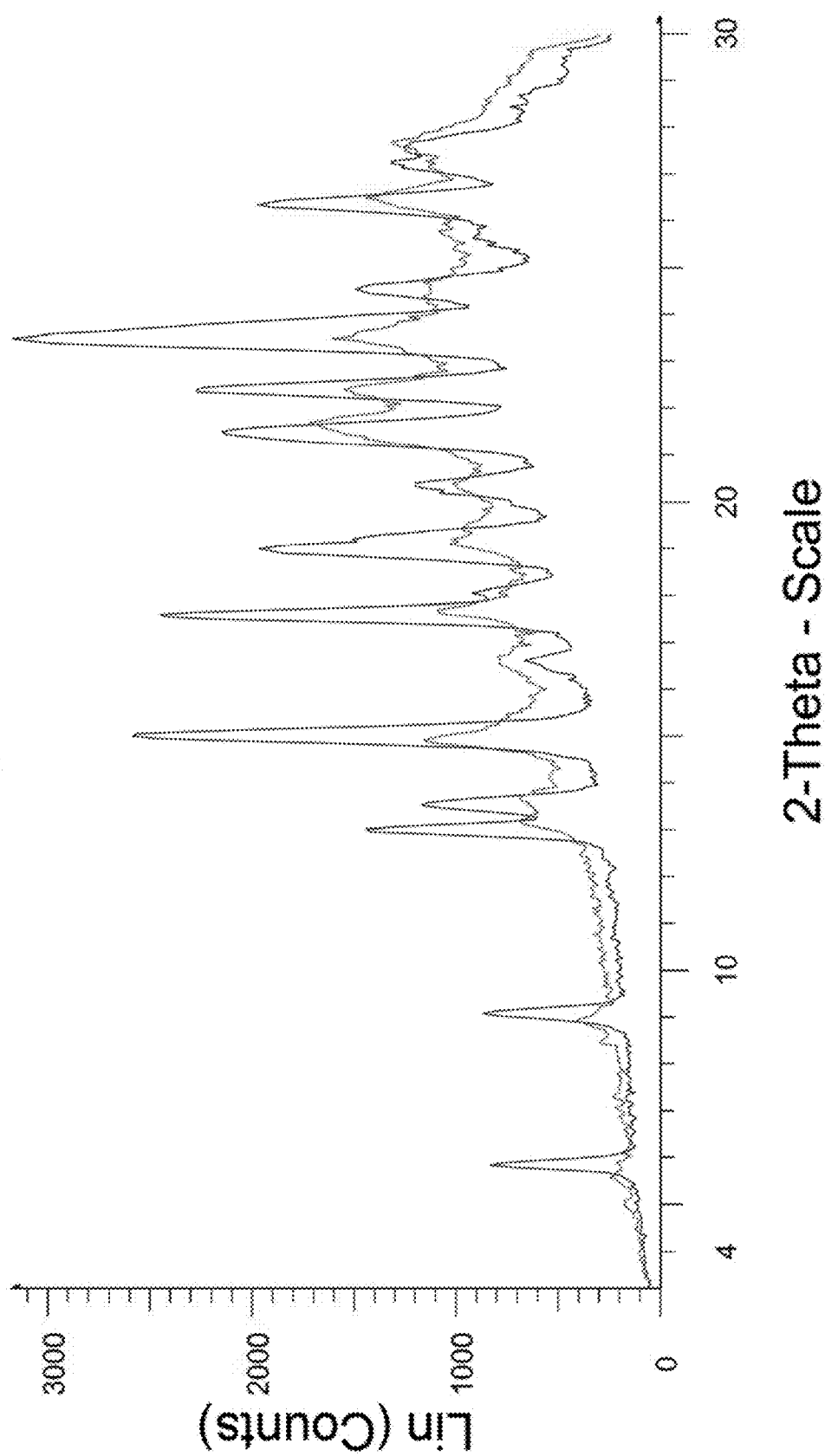
FIG. 7 shows XRPD analysis of crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide after synthesis and after storage for 7 days at 40° C. and 75% RH.

In certain embodiments, the crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide has an XRPD pattern substantially as illustrated in FIG. 7 after synthesis of the crystalline salt.

In a preferred embodiment, the crystalline mono sulfate salt has characteristic peaks at diffraction angle 2-theta degrees appearing at least at about 15, about 17.8 and about 23.5, as measured by XRPD. In a more preferred embodiment, the crystalline mono sulfate salt has characteristic peaks at diffraction angle 2-theta degrees appearing at least at about 15, about 17.8, about 22.5 and about 23.5, as measured by XRPD. In a still more preferred embodiment, the crystalline mono sulfate salt has characteristic peaks at diffraction angle 2-theta degrees appearing at least at about 15, about 17.8, about 19.0, about 22.5 and about 23.5, as measured by XRPD.

Figure 8:
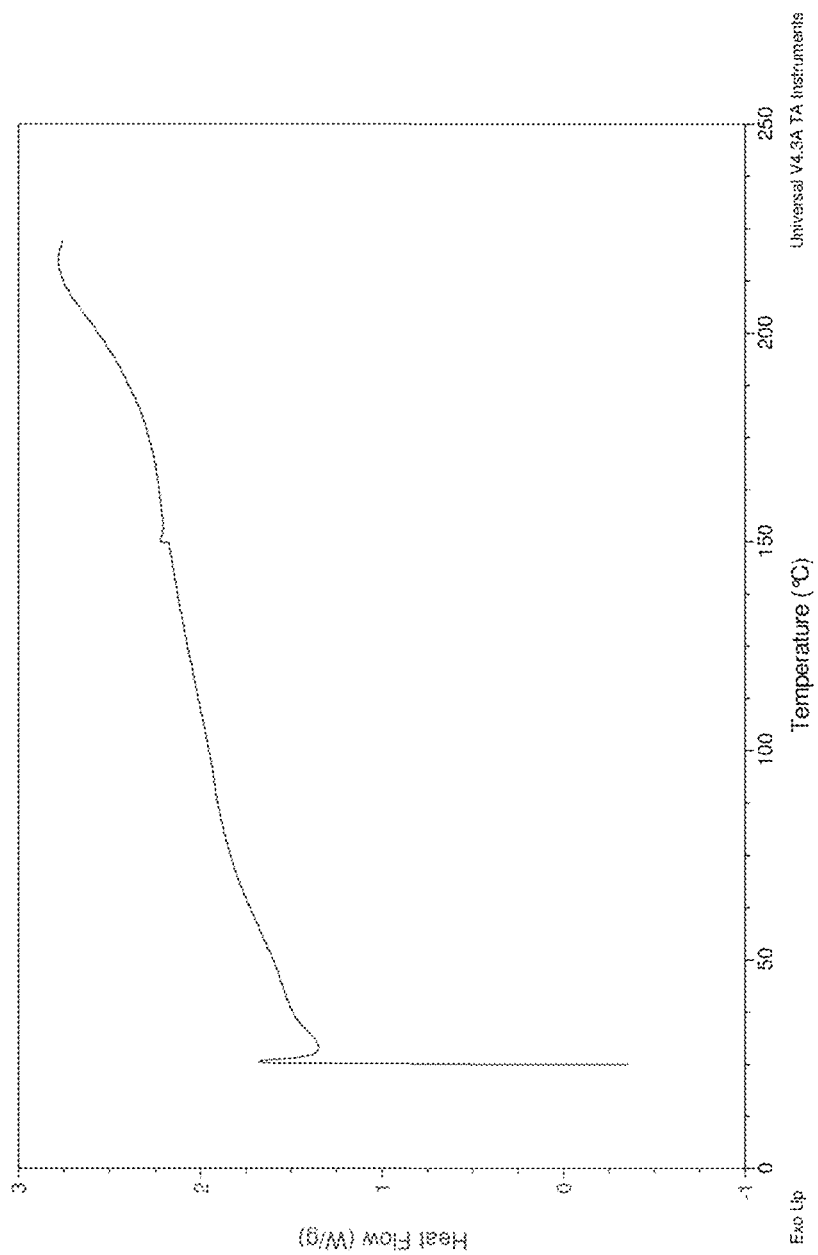
FIG. 8 is a DSC curve of crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4, 4a,5,5a,6,11,12a-octahydro-naphthacene-2-carboxylic acid amide after synthesis.

In a certain embodiment, the crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide exhibits a DSC curve substantially as illustrated in FIG. 8. Preferably, the crystalline mono sulfate salt analyzed by DSC exhibits no events up to degradation of the crystalline salt.

Figure 9:
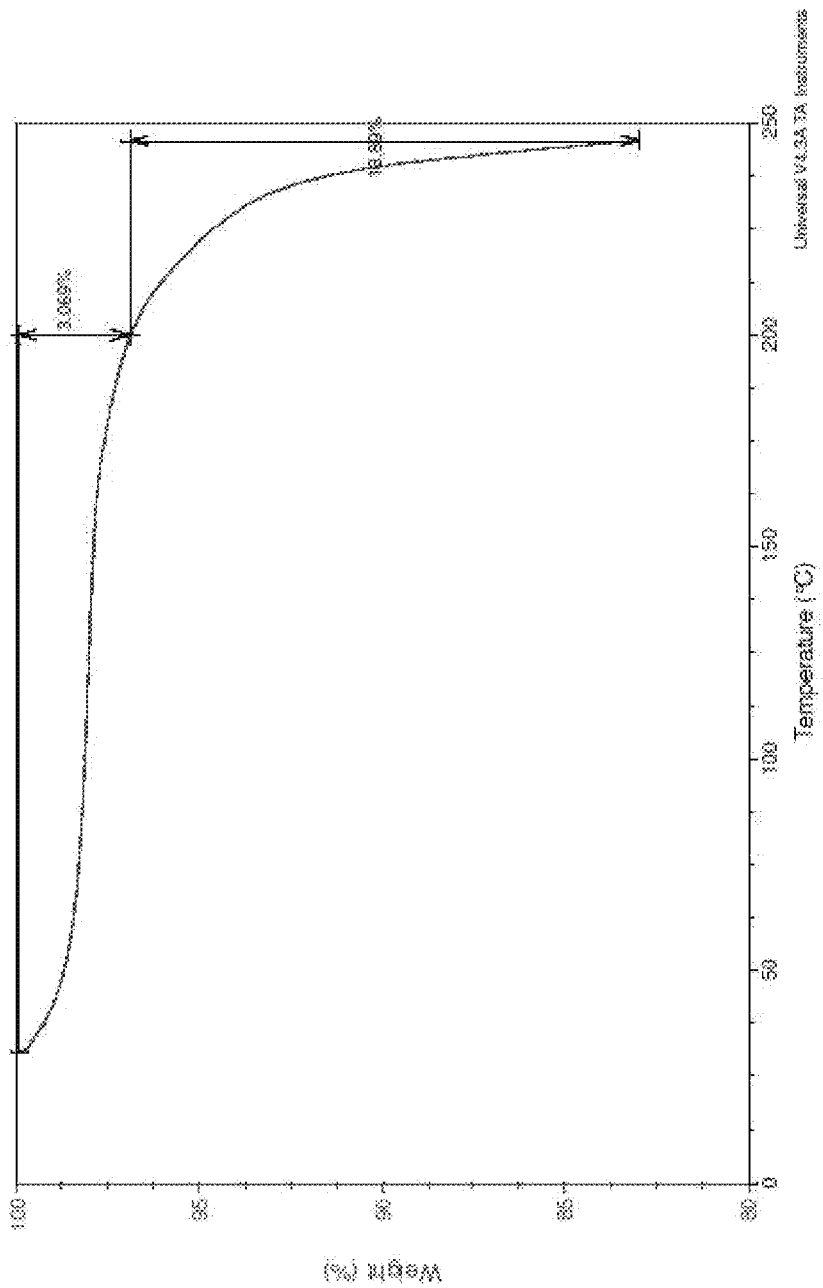
FIG. 9 is a TGA of crystalline mono sulfate salt of (4S,4aS, 5aR,12aS)-4-dimethylamino-3,10,12,12a-tetrahydroxy-7-[(methoxy(methyl)amino)-methyl]-1,11-dioxo-1,4,4a,5,5a, 6,11,12a-octahydro-naphthacene-2-carboxylic acid amide after synthesis.

In a certain embodiment, the crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide exhibits a TGA curve substantially as illustrated in FIG. 9. Preferably, the crystalline mono sulfate salt analyzed by TGA exhibits a weight loss of about 1% to about 5% from about 30° C. to about 200° C. and a weight loss of about 12% to about 16% from about 200° C. to about 250° C. and, more preferably, a weight loss of about 3% to about 4% from about 30° C. to about 200° C. and a weight loss of about 13% to about 14% from about 200° C. to about 250° C.

In a certain embodiment of the present invention, the crystalline mono sulfate salt of (4S,4aS,5aR,12aS)-4-dimethylamino-3,10,12,12a-tetrahydroxy-7-[(methoxy(methyl) amino)-methyl]-1,11-dioxo-1,4,4a,5,5a,6,11,12a-octahydro-naphthacene-2-carboxylic acid amide is stable and has a β-isomer content after storage for about 75 days at about 40° C. and about 75% RH not more than about 20% peak area greater than the β-isomer content at about 0 days. In a preferred embodiment, the salt has a β-isomer content after storage for about 75 days at about 40° C. and about 75% RH not more than about 10% peak area greater than the β-isomer content at about 0 days; in a more preferred embodiment, the β-isomer content after storage for about 75 days at about 40° C. and about 75% RH is not more than about 1% peak area greater than the β-isomer content at about 0 days; and in a further preferred embodiment, the β-isomer content after storage for about 75 days at about 40° C. and about 75% RH is about equal to the β-isomer content at about 0 days.

In a certain embodiment, the β-isomer content of the crystalline mono sulfate salt of (4S,4aS,5aR,12aS)-4-dimethylamino-3,10,12,12a-tetrahydroxy-7-[(methoxy(methyl) amino)-methyl]-1,11-dioxo-1,4,4a,5,5a,6,11,12a-octahydro-naphthacene-2-carboxylic acid amide at 0 days is about 3.0% to about 26.0% peak area, preferably about 5.0% to about 20.0% peak area, and most preferably about 6.0% to about 10.0% peak area.

Pharmaceutical Compositions

One embodiment of the invention is directed to a pharmaceutical composition comprising a crystalline salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, wherein the salt is selected from a group consisting of mono hydrochloride, mono mesylate, and mono sulfate, and a pharmaceutically acceptable excipient.

The pharmaceutical composition of the present invention comprises an effective amount of a crystalline salt, a pharmaceutically acceptable excipient, and, in some embodiments, it may also contain one or more additional active ingredients. The content of crystalline salt in the pharmaceutical composition of the present invention varies depending on the subject of administration, route of administration and target disease, among other variables. The pharmaceutical composition of the present invention may be administered orally, topically (e.g., transdermal, etc.), vaginally, rectally, or parenterally (e.g., intravenous, etc.). Preferably, the pharmaceutical composition of the present invention may be used for treating bacterial infections and inflammatory skin disorders. For example, the pharmaceutical composition of the present invention may be used for treating acne and/or rosacea, e.g., for treating acne, or for treating infections with gram positive bacteria, wherein the gram positive bacteria is selected from the group consisting of *Propionibacterium acnes, Staphylococcus aureus, Streptococcus pneumonia, Streptococcus pyogenes*, and *Clostridium difficile*.

Examples of topical administration of the pharmaceutical composition include transdermal, buccal or sublingual application. For topical applications, the pharmaceutical composition can be suitably admixed in a pharmacologically inert topical carrier, such as a gel, an ointment, a lotion or a cream. Such pharmacologically inert topical carriers include water, glycerol, alcohol, propylene glycol, fatty alcohols, triglycerides, fatty acid esters, or mineral oils. Other possible pharmacologically inert topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added.

For oral administration, the crystalline salt of the present invention may be administered as a capsule, tablet or granule. Tablets may contain various excipients such as microcrystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinylpyrrolidone, sucrose, gelatin and acacia. In a certain embodiment, the tablet may be film coated. Additionally, lubricating agents such as magnesium stearate, sodium lauryl sulfate and talc are often very useful for tablets. Other solid compositions may also be employed as fillers in gelatin capsules; preferred materials in this connection also include lactose or milk sugar as well as high molecular weight polyethylene glycols. When aqueous suspensions and/or elixirs are desired for oral administration, the crystalline salt may be combined with various sweetening or flavoring agents, coloring matter or dyes, and, if so desired, emulsifying and/or suspending agents, together with such diluents as water, ethanol, propylene glycol, glycerin and various like combinations thereof. The pharmaceutical compositions of the invention may be formulated such that the crystalline salt is released over a period of time after administration.

Preparing such pharmaceutical compositions of the crystalline salt of the present invention along with a pharmaceutically acceptable excipient and, optionally, an additional active ingredient, may be done by any conventional technique known in the art.

In an embodiment, the crystalline salt present in the pharmaceutical composition is about 0.01% to about 90% by weight relative to the whole composition. A suitable therapeutically effective amount of the crystalline salt will typically range from about 0.01 mg/kg to about 1 g/kg of body weight per day; in another embodiment, from about 1 mg/kg to about 600 mg/kg body weight per day; in another embodiment, from about 1 mg/kg to about 250 mg/kg body weight per day; in another embodiment, from about 10 mg/kg to about 400 mg/kg body weight per day; in another embodiment, from about 10 mg/kg to about 200 mg/kg of body weight per day; in another embodiment, from about 10 mg/kg to about 100 mg/kg of body weight per day; in one embodiment, from about 10 mg/kg to about 25 mg/kg body weight per day; in another embodiment, from about 1 mg/kg to about 10 mg/kg body weight per day; in another embodiment, from about 0.001 mg/kg to about 100 mg/kg of body weight per day; in another embodiment, from about 0.001 mg/kg to about 10 mg/kg of body weight per day; and in another embodiment, from about 0.001 mg/kg to about 1 mg/kg of body weight per day. In a certain embodiment, when a pharmaceutical composition described herein is administered orally, a suitable therapeutically effective amount of the crystalline salt is about 0.01 to about 100 milligrams per kilogram of body weight of recipient per day, preferably about 0.1 to about 50 milligrams per kilogram body weight of recipient per day, more preferably from about 0.1 to about 20 milligrams per kilogram body weight of recipient per day, and even more preferably from about 0.1 to about 10 milligrams per kilogram body weight of recipient per day. The desired dose may be administered once daily, or by several sub-divided doses, e.g., 2 to 5 sub-divided doses, at appropriate intervals through the day, or other appropriate schedule.

The term "pharmaceutically acceptable excipient" as used herein includes, but is not limited to, one of more of the following: polymers, resins, plasticizers, fillers, lubricants, diluents, binders, disintegrants, solvents, co-solvents, surfactants, buffer systems, preservatives, sweetener agents, flavoring agents, pharmaceutical-grade dyes or pigments, chelating agents, viscosity agents, and combinations thereof. Pharmaceutically acceptable excipients can be used in any component in making the dosage form, i.e. core tablet or coating. Flavoring agents and dyes and pigments among those useful herein include but are not limited to those described in Handbook of Pharmaceutical Excipients (4th Ed., Pharmaceutical Press 2003). Suitable co-solvents include, but are not limited to, ethanol, isopropanol, acetone, and combinations thereof. Suitable surfactants include, but are not limited to, polyoxyethylene sorbitan fatty acid esters, polyoxyethylene monoalkyl ethers, sucrose monoesters, simethicone emulsion, sodium lauryl sulfate, TWEEN 80® (polyethylene sorbitol ester), and lanolin esters, ethers, and combinations thereof. Suitable preservatives include, but are not limited to, phenol, alkyl esters of parahydroxybenzoic acid, benzoic acid and the salts thereof, boric acid and the salts thereof, sorbic acid and the salts thereof, chlorbutanol, benzyl alcohol, thimerosal, phenylmercuric acetate and nitrate, nitromersol, benzalkonium chloride, cetylpyridinium chloride, methyl paraben, propyl paraben, and combinations thereof. Suitable fillers include, but are not limited to, starch, lactose, sucrose, maltodextrin, and microcrystalline cellulose. Suitable plasticizers include, but are not limited to, triethyl citrate, polyethylene glycol, propylene glycol, dibutyl phthalate, castor oil, acetylated monoglycerides, triacetin, and combinations thereof. Suitable polymers include, but are not limited to, ethylcellulose, cellulose acetate trimellitate, hydroxypropylmethylcellulose phthalate, cellulose acetate phthalate, polyvinyl acetate phthalate, and EUDRAGIT® L 30-D (poly(methacrylic acid-co-ethyl acrylate) 1:1), EUDRAGIT® L 100-55 (poly(methacrylic acid-co-ethyl acrylate) 1:1), EUDRAGIT® FS30D (poly(methylacrylate-co-methyl methcrylate-co-methacrylic acid) 7:3:1) and EUDRAGIT® S 100 (poly(methacrylic acid-co-methylacrylate) 1:2), (Rohm Pharma GmbH and Co. KG, Darmstadt, Germany), ACRYL-EZE® (poly(methacrylic acid-co-ethyl acrylate) 1:1); and SURETERIC® (poly-vinylacetate phthalate) (Colorcon, Inc., West Point, Pa.), and combinations thereof. Suitable lubricants include, but are not limited to, magnesium stearate, stearic acid, talc, and combinations thereof.

The improved stability of the crystalline salts of the present invention means that the crystals are less hygroscopic, i.e., less sensitive to humidity, so that a pharmaceutical composition containing the crystalline salt can be stored for a longer period of time than previously known pharmaceutical compositions.

In a certain embodiment, the pharmaceutical composition comprises the mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide and a pharmaceutically acceptable excipient. In another embodiment, the pharmaceutical composition comprises the mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide and a pharmaceutically acceptable excipient. In a still further embodiment, the pharmaceutical composition comprises the mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide and a pharmaceutically acceptable excipient.

In a certain embodiment, the invention is directed to a pharmaceutical composition comprising (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, or a pharmaceutically acceptable salt thereof and a pharmaceutically acceptable excipient for use in treating a bacterial infection, e.g., a *Streptococcus pyogenes* and *Clostridium difficile* bacterial infection. In a preferred embodiment, the pharmaceutical composition comprises a crystalline salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide selected from the group consisting of mono hydrochloride, mono mesylate and mono sulfate salt.

The phrase "pharmaceutically acceptable salt" of a compound as used herein means a salt that is pharmaceutically acceptable and that possesses the desired pharmacological activity of the parent compound. Pharmaceutically acceptable salts include salts of acidic or basic groups present in a compound of the invention. Pharmaceutically acceptable acid addition salts include, but are not limited to, hydrochloride, hydrobromide, hydroiodide, nitrate, mesylate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate and pamoate (i.e., 1,1'-methylene-bis-(2-hydroxy-3-naphthoate)) salts. Suitable base salts include, but are not limited to, aluminum, calcium, lithium, magnesium, potassium, sodium, zinc, and diethanolamine salts. Preferably, the pharmaceutically acceptable salt is a crystalline salt. Even more preferably, the pharmaceutically acceptable salt is a crystalline salt selected from mono hydrochloride, mono mesylate, and mono sulfate.

Methods of Use

One embodiment of the invention is directed to a method for treating acne and/or rosacea comprising administering to a subject a therapeutically effective amount of a crystalline salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, wherein the crystalline salt is selected from a group consisting of mono hydrochloride, mono mesylate and mono sulfate. In one embodiment, the invention is directed to a method of treating acne. In another embodiment, the invention is directed to a method of treating rosacea.

The term "treating" as used herein includes therapeutic and/or prophylactic treatment of acne and/or rosacea or other conditions described herein. The treatment includes the diminishment or alleviation of at least one symptom associated with acne and/or rosacea or at least one symptom associated with another condition described herein.

The term "therapeutically effective amount" as used herein means an amount of a compound or composition high enough to significantly positively modify the symptoms and/or condition to be treated, but low enough to avoid serious side effects (at a reasonable risk/benefit ratio), within the scope of sound medical judgment. The therapeutically effective amount of active ingredient for use in the method of the invention herein will vary with the particular condition being treated, the age and physical condition of the patient to be treated, the severity of the condition, the duration of the treatment, the nature of concurrent therapy, the particular active ingredient being employed, the particular pharmaceutically-acceptable excipients utilized, and like factors within the knowledge and expertise of a skilled physician or veterinarian. Various suitable therapeutically effective amounts are described above.

The term "subject" as used herein is an animal "Subject" includes, without limitation, a human, mouse, rat, guinea pig, dog, cat, horse, cow, pig, monkey, chimpanzee, baboon, or rhesus monkey. In one embodiment, "subject" is a mammal. In another embodiment, "subject" is a human.

A certain embodiment is directed to the method for treating acne comprising administering to a subject a therapeutically effective amount of the crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide. In an embodiment thereof, the amount of the mono hydrochloride salt employed is between about 10 mg and about 2000 mg, and preferably between about 25 mg and about 500 mg. In a certain embodiment, the mono hydrochloride salt is administered at least once monthly, preferably, weekly, more preferably, bi-weekly, and most preferably, the mono hydrochloride salt is administered daily.

Another embodiment is directed to the method for treating acne comprising administering to a subject a therapeutically effective amount of the crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide. In certain embodiments thereof, the amount of crystalline mono mesylate salt employed is between about 10 mg and about 2000 mg, and preferably between about 25 mg and about 500 mg. In a certain embodiment, the mono mesylate salt is administered at least once monthly, preferably, weekly, more preferably, bi-weekly, and most preferably, the mono mesylate salt is administered daily.

A further embodiment is directed to the method for treating acne comprising administering to a subject a therapeutically effective amount of the crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide. In certain embodiments, the amount of crystalline mono sulfate salt employed is between about 10 mg and about 2000 mg, and preferably between about 25 mg and about 500 mg. In a certain embodiment, the mono sulfate salt is administered at least once monthly, preferably, weekly, more preferably, bi-weekly, and most preferably, the mono sulfate salt is administered daily.

Yet another embodiment of the invention is directed to a method of treating a gram positive bacterial infection comprising administering to a subject a therapeutically effective amount of a crystalline salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, wherein the crystalline salt is selected from a group consisting of mono hydrochloride, mono mesylate and mono sulfate. Gram positive bacterial infections include *Propionibacterium acnes*, *Staphylococcus aureus*, *Streptococcus pneumonia*, *Streptococcus pyogenes*, and *Clostridium difficile* infections.

An additional embodiment of the invention is directed to a method of treating a bacterial infection, e.g., a gram positive bacterial infection selected from *Streptococcus pyogenes* and *Clostridium difficile* infection, comprising administering to a subject a therapeutically effective amount of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide or pharmaceutically acceptable salt thereof. In a preferred embodiment, the method comprises administering to a subject a therapeutically effective amount of a crystalline salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, preferably the salt is mono hydrochloride, mono mesylate or mono sulfate salt.

The following examples will illustrate the practice of the present invention in some of the preferred embodiments. Other embodiments within the scope of the claims will be apparent to one skilled in the art.

EXAMPLES

The following examples illustrate the synthesis of the compounds described herein.

Synthesis of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide ("the free base")

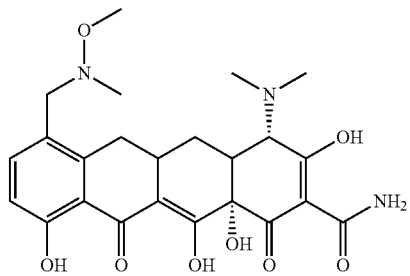 [SMILES: CON(C)Cc1ccc(O)c2c1CC1CC3[C@H](N(C)C)C(O)=C(C(N)=O)C(=O)[C@@]3(O)C(O)=C1C2=O]

A solution of 7-formylsancycline TFA salt (2.23 g) and N,O-dimethylhydroxylamine hydrochloride (780 mg) in N,N-dimethylacetamide (15 mL) was stirred for 10 minutes at room temperature under argon atmosphere. To this solution was added sodium cyanoborohydride (302 mg). The solution was stirred for 5 minutes and monitored by LC-MS. The reaction mixture was poured into diethyl ether, and the resulting precipitates were collected by filtration under vacuum. The crude product was purified by prep-HPLC using a C18 column (linear gradient 10-40% acetonitrile in 20 mM aqueous triethanolamine, pH 7.4). The prep-HPLC fractions were collected, and the organic solvent (acetonitrile) was evaporated under reduced pressure. The resulting aqueous solution was loaded onto a clean PDVB SPE column, washed with distilled water, then with a 0.1 M sodium acetate solution followed by distilled water. The product was eluted with acetonitrile. The eluent was concentrated under reduced pressure, 385 mg was obtained as free base.

Synthesis of crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide (the "Crystalline Mono Hydrochloride Salt")

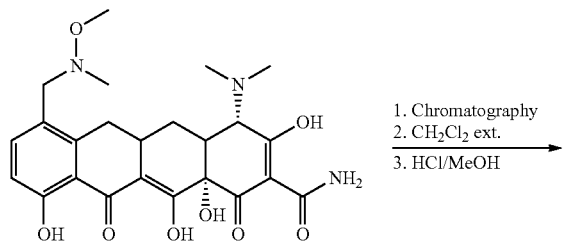

1. Chromatography
2. CH$_2$Cl$_2$ ext.
3. HCl/MeOH

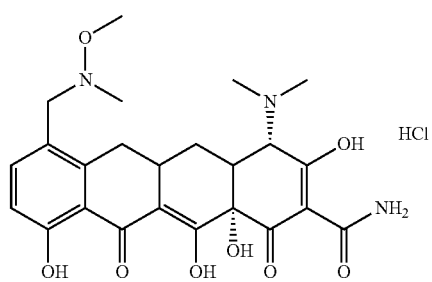

Crude (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide (100 g, app. 35% assay) was purified on preparative column chromatography. The desired fractions (8-10 liters) were combined and the pH was adjusted to 7.0-7.5 using ammonium hydroxide. This aqueous solution was extracted 3 times with dichloromethane (4 liters each time). The dichloromethane layers were combined and concentrated under reduced pressure. The residue was suspended in ethanol (800 ml) and 20 ml water was added. The pH was gradually adjusted to pH 1.6-1.3 using 1.25M hydrochloric acid in methanol and the mixture was stirred for 20-60 minutes at which point the free base was completely dissolved. The solution was concentrated under reduced pressure to 200-250 ml and was seeded with (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide mono HCl crystals (100-200 mg). The stirring was continued for 2-18 hours while the slurry was kept at ≤5° C. The resulting crystals were filtered, washed with ethanol (50 mL) and dried under reduced pressure to a constant weight. 20 g crystalline (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide mono hydrochloride was isolated in ≥90% purity and ≥90% assay.

Synthesis of crystalline mono mesylate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid (the "Crystalline Mesylate Salt")

(4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide free base (74 mg) was suspended in ethanol (740 μl) and heated with stirring to 60° C. (bath temperature). Methane sulfonic acid (1.1 eq, 167 μl as 1M solution in THF) was added and most of the solid dissolved. After five minutes, the suspension was cooled to ambient temperature over approximately 1.75 hours (uncontrolled in oil bath). By 53° C., solid had precipitated which was filtered at ambient temperature under reduced pressure. A further portion of ethanol (200 μl) was added to aid filtration, as the suspension was viscous. The cake was washed with n-hexane (400 μl) and air dried on filter for approximately 30 minutes to yield 59 mg (67% yield) of yellow solid.

Synthesis of crystalline mono sulfate salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid (the "Crystalline Sulfate Salt")

(4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide free base (86 mg) was suspended in ethanol (500 μl) and heated with stirring to 63° C. (bath temperature) at which temperature most of the free base had dissolved. Sulfuric acid (1.1 eq, 194 μl as 1M solution in water) was added and all of the solid dissolved. The solution was cooled to ambient temperature over approximately 1.75 hours (uncontrolled in oil bath) at which temperature no solid had precipitated. Methyl t-butyl ether (MtBE) was added as an antisolvent (4×50 μl). Each addition caused a cloud point, but the solid re-dissolved on stirring. The solution was stirred with a stopper for approximately 3 hours after which time solid precipitated. The solid was filtered under reduced pressure and washed with MtBE (3×200 μl) and air dried on filter for approximately 45 minutes to yield 93 mg (90% yield) of yellow solid.

Comparative Example 1

Figure 10:
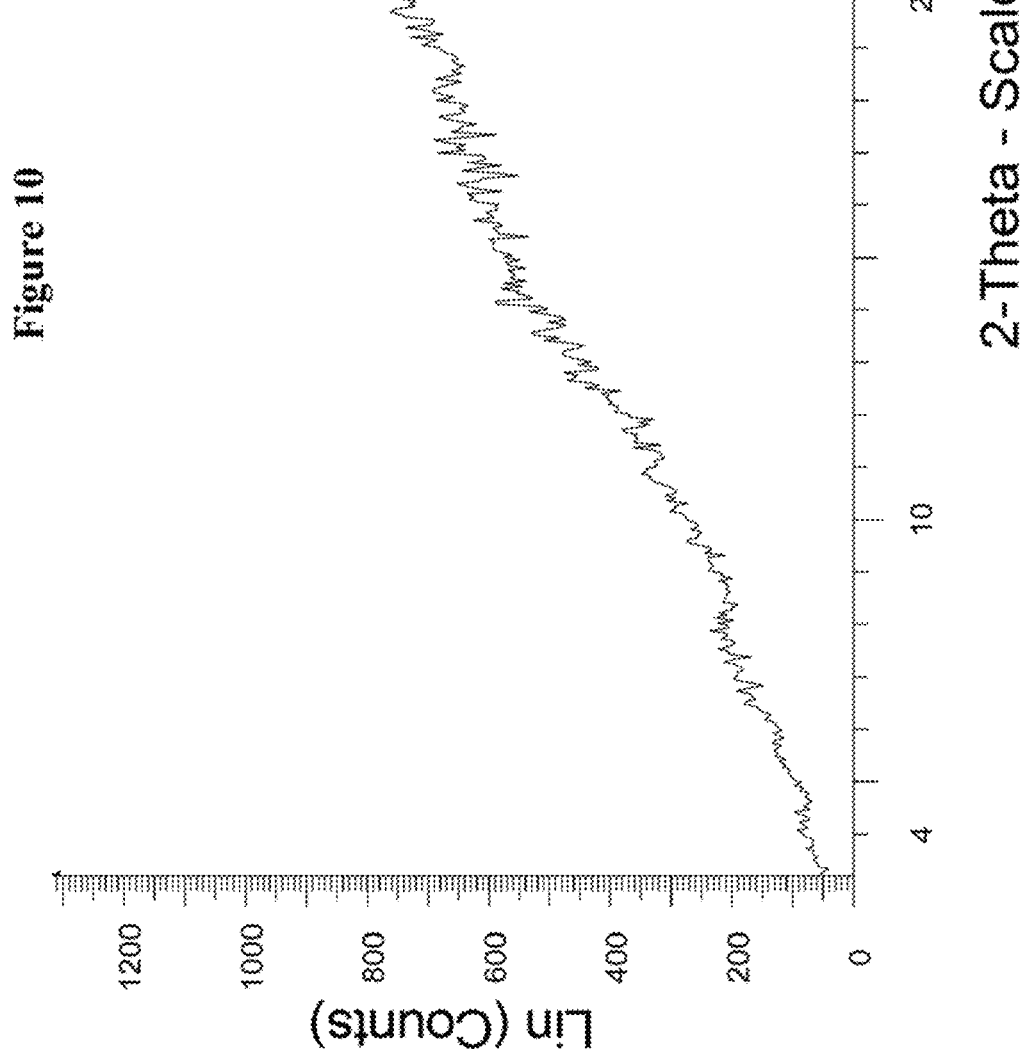
FIG. 10 shows XRPD analysis of amorphous bis hydrochloride salt of (4S,4aS,5aR,12aS)-4-dimethylamino-3,10, 12,12a-tetrahydroxy-7-[(methoxy(methyl)amino)-methyl]-1,11-dioxo-1,4,4a,5,5a,6,11,12a-octahydro-naphthacene-2-carboxylic acid amide.
Figure 11:
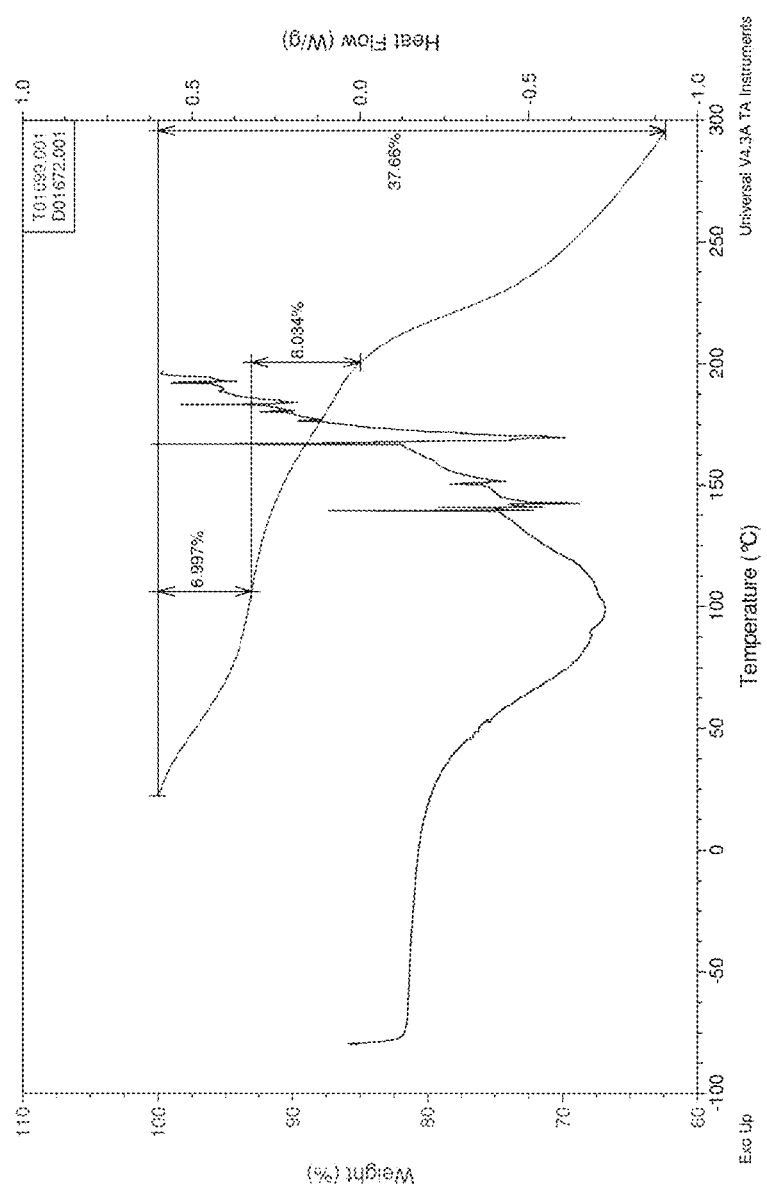
FIG. 11 is a TGA curve and DSC curve overlaid of amorphous bis hydrochloride salt of (4S,4aS,5aR,12aS)-4-dimethylamino-3,10,12,12a-tetrahydroxy-7-[(methoxy(methyl) amino)-methyl]-1,11-dioxo-1,4,4a,5,5a,6,11,12a-octahydro-naphthacene-2-carboxylic acid amide.

Synthesis of amorphous bis hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide free base (1 g) was suspended in methanol (50 mL). The freebase was converted to the hydrochloride salt by adding an excess of methanolic HCl followed by under reduced pressure evaporation to give 1.1 g yellow solid: MS (Mz+1=488). $^1$H NMR (300 MHz, CD3OD) δ 7.46 (d, 1H, J=8.6 Hz), 6.81 (d, 1H, J=8.6 Hz), 4.09 (d, 1H, J=1.0 Hz), 3.79 (d, 1H, J=13.1 Hz), 3.73 (d, 1H, J=13.1 Hz), 3.36 (m, 1H), 3.27 (s, 3H), 3.08-2.95 (8H), 2.61 (s, 3H), 2.38 (t, 1H, J=14.8), 2.22 (m, 1H), 1.64 (m, 1H). An XRPD pattern is shown in FIG. 10 and a TGA and DSC curve overlaid are shown in FIG. 11.

Comparative Example 2

Synthesis of amorphous mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide A sample of Crystalline Mono Hydrochloride Salt (2.09 g) was dissolved in water (250 ml, 120 vols), filtered and frozen in a −78° C. bath. Water was removed from the solidified sample using a lyophilizer for 110 hours to yield the amorphous mono hydrochloride salt as a fluffy yellow solid, that was confirmed to be amorphous by XRPD analysis Testing In order to determine the stability of Crystalline Mono Hydrochloride Salt, the β-isomer content of the salt was determined by HPLC-UV analysis and compared to the β-isomer content calculated after the salt was stored in an amber glass vial for approximately 75 days at ambient conditions. The results are shown in Table 1 below. As evidenced by the data collected, the β-isomer content did not increase over time and therefore, storage did not negatively affect the chemical purity of the Crystalline Mono Hydrochloride Salt.

TABLE 1

Formation of β-isomer in the Crystalline Mono Hydrochloride Salt after Storage.

| Sample | Chemical Purity at 0 days | Chemical Purity at 75 days |
|---|---|---|
| Crystalline Mono Hydrochloride Salt | 93.8% (3.8% β-isomer) | 94.8% (3.8% β-isomer) |

Other samples of the Crystalline Mono Hydrochloride Salt were analyzed by HPLC-UV and due to minor variations in the synthetic process, purity at 0 days was found to be 93.8% (3.5% β-isomer) and 95.8% (3.4% β-isomer). The chemical purity for these samples after storage was not tested.

Further evidence of stability was demonstrated by analysis of the total impurity content of Crystalline Mono Hydrochloride Salt by HPLC-UV at 0 days and again after storage for about 6 months at about 40° C. and about 75% RH and was found to be 4% peak area and 6% peak area, respectively.

In tests conducted on the stability of Comparative Example 1, after just 48 hours of storage at about 40° C. and about 75% RH, the β-isomer content increased to 31.7% peak area from 3.6% peak area at 0 days. After storage for 36 days at about 25° C. and about 60% RH, the β-isomer content was calculated as 8.7% peak area. In another test, the compound of Comparative Example 1 had a total impurity content of 4.2% peak area at 0 days and 34.6% peak area after storage for about 2 days at about 40° C. and about 75% RH. Accordingly, Comparative Example 1 exhibited a much higher increase in total impurity content and was significantly less stable than Crystalline Mono Hydrochloride Salt.

The β-isomer content of Comparative Example 2 was also determined by HPLC-UV analysis at 0 days and compared to the β-isomer content calculated after the compound was stored in a clear glass vial for approximately 75 days at ambient conditions. The results are shown in Table 2 below. As evidenced by the data, after storage for 75 days, the β-isomer content increased by over 80% and, therefore, the storage negatively affected the chemical purity of Comparative Example 2.

TABLE 2

Formation of β-isomer in Comparative Example 2 after Storage.

| Sample | Chemical Purity at 0 days | Chemical Purity at 75 days |
|---|---|---|
| Comparative Example 2 | 94.3% (4.4% β-isomer) | 90.4% (7.8% β-isomer) |

The stability of Crystalline Mono Hydrochloride Salt was compared to the amorphous mono hydrochloride salt of Comparative Example 2. The results of various tests demonstrating advantages and disadvantages of the Crystalline Mono Hydrochloride Salt and Comparative Example 2 are shown in Table 3 below.

TABLE 3

Advantages and Disadvantages of the Crystalline Mono Hydrochloride Salt and Comparative Example 2.

| Solid form | Advantages | Disadvantages |
|---|---|---|
| Crystalline Mono Hydrochloride Salt | Non hygroscopic to 90% RH | Some loss of crystallinity upon pressing and milling |
| | No change in form or β-isomer content upon milling or pressing | — |
| | No increase in β-isomer content upon storage under ambient conditions | — |
| Comparative Example 2 | High glass transition (166° C.) | Hygroscopic above 70% RH |
| | Stable to crystallization upon storage and heat/cool cycle | Change in form (from amorphous to crystalline) to Crystalline Mono Hydrochloride Salt observed above 75% RH |
| | — | Increase in β-isomer content upon storage at 63% RH |
| | — | Increase in β-isomer content upon pressing and milling |
| | — | Increase in β-isomer content upon storage under ambient conditions |
| | — | Faster rate of β-isomer formation upon exposure to solvent as compared to Crystalline Mono Hydrochloride Salt |

HPLC-UV and XRPD analysis were conducted on samples of Crystalline Mono Hydrochloride Salt, Crystalline Mesylate Salt and Crystalline Sulfate Salt at 0 days and after storage for 7 days at 40° C. and 75% RH. FIGS. 1, 4 and 7 show the XRPD analysis of the Crystalline Mono Hydrochloride Salt, Crystalline Mesylate Salt and Crystalline Sulfate Salt at 0 days and after storage at 40° C. and 75% RH with the graphs overlaid for comparison. As shown in FIG. 1, Crystalline Mono Hydrochloride Salt showed no change in crystal form after storage. As shown in FIG. 4, Crystalline Mesylate Salt also showed no change in crystal form after storage. The changes shown in the figure are in intensity and resolution rather than in peak position, which, if present, would indicate change in crystal form. Accordingly, Crystalline Mono Hydrochloride Salt and Crystalline Mesylate Salt are physically stable, as shown by FIGS. 1 and 4. As shown in FIG. 7, Crystalline Sulfate Salt showed increased crystalline content after storage.

The results of HPLC-UV analysis for the same samples of Crystalline Mesylate Salt and Crystalline Sulfate Salt are shown in Table 4. As the β-isomer content did not increase after storage, these salts were not negatively affected by storage.

TABLE 4

Formation of β-isomer in Crystalline Mesylate Salt and Crystalline Sulfate Salt after Storage.

| Sample | Chemical Purity at 0 days | Chemical Purity at 7 days, 40° C. and 75% RH |
|---|---|---|
| Crystalline Mesylate Salt | 92% (3% β-isomer) | 98% (2% β-isomer) |
| Crystalline Sulfate Salt | 88% (9% β-isomer) | 91% (9% β-isomer) |

In addition, differential scanning calorimetry (DSC) and thermo-gravimetric (TGA) analysis of Crystalline Mono Hydrochloride Salt, Crystalline Mesylate Salt and Crystalline Sulfate Salt after synthesis was conducted. The DSC curves are shown in FIGS. 2, 5 and 8 and the TGA curves are shown in FIGS. 3, 6 and 9. These figures show that, by DSC analysis, there are no events up to degradation of the salts, thereby, confirming stability of the salts at raised temperatures. The TGA curves show that no hydrates or solvates were present. The observed apparent weight loss is due to instability of the machine.

Table 5 below presents the results of DSC and TGA analysis of the crystalline salts of the present invention, the crystalline free base and Comparative Example 1.

TABLE 5

DSC and TGA Analysis of Crystalline Mono Hydrochloride Salt, Crystalline Mesylate Salt and Crystalline Sulfate Salt, Crystalline Free Base and Comparative Example 1.

| Sample | Differential Scanning Calorimetry | Thermo-Gravimetric Analysis |
|---|---|---|
| Crystalline Mono Hydrochloride Salt | No events up to degradation | 3% weight loss from about 30° C. to about 200° C. 14% weight loss from about 200° C. to about 250° C. |
| Crystalline Mesylate Salt | No events up to degradation | 3% weight loss from about 30° C. to about 200° C. 7% weight loss from about 200° C. to about 250° C. |
| Crystalline Sulfate Salt | No events up to degradation | 3% weight loss from about 30° C. to about 200° C. 14% weight loss from about 200° C. to about 250° C. |
| Crystalline Free Base | Endothermic peak at 175° C. (ΔH 72 J·g$^{-1}$) | 15% weight loss from about 30° C. to decomposition at less than 220° C. |
| Comparative Example 1 | Broad endothermic peak between about 20° C. and about 200° C. | 7% weight loss from about 30° C. to about 106° C. 8% weight loss from about 106° C. to about 200° C. 23% weight loss from about 200° C. to about 300° C. |

Accordingly, Crystalline Mono Hydrochloride Salt, Crystalline Mesylate Salt and Crystalline Sulfate Salt are more stable than Comparative Example 1.

Antimicrobial Activity

Antimicrobial activity of the Crystalline Mono Hydrochloride Salt was assessed according to anti-anaerobic activity, mechanism of action and in vivo efficacy studies as detailed herein. Whether either amorphous bis hydrochloride salt or crystalline mono hydrochloride salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide is used to prepare samples for these studies, it is well understood in the art that efficacy data would be the same for all salt forms, since the compound is placed into solution prior to testing. Accordingly, whether starting with the Crystalline Mono Hydrochloride Salt or amorphous bis hydrochloride salt of (4S,4aS,5aR,12aS)-4-dimethylamino-3,10,12,12a-tetrahydroxy-7-[(methoxy(methyl)amino)-methyl]-1,11-dioxo-1,4, 4a,5,5a,6,11,12a-octahydro-naphthacene-2-carboxylic acid amide, the free base (as defined above; herein "the active") is what is being tested.

For the studies below, samples were prepared with bis hydrochloride salt, and the data is expressed based on the free base ("active"). The overall anti-anaerobic microbial activity of the Crystalline Mono Hydrochloride Salt can be seen via in vitro study of the active against 37 representative strains of anaerobic bacteria and the results compiled in Table 6. The active demonstrated relatively potent activity (i.e., minimum inhibitory concentration (MIC) of 4 µg/mL or less) against many species of Gram-positive bacteria, including *P. acnes*. Overall, the activity of the active was similar to that of tetracycline and doxycycline but less than that of minocycline. Organisms with high MIC values for the active (MIC≥16 µg/mL) included *C. perfringens* and *S. constellatus*.

MIC values for the Gram-negative anaerobes are shown in Table 6. The tetracycline-resistant strains were cross-resistant to the active. The active and the other tetracyclines demonstrated potent activity against *E. corrodens* and *Fusobacterium* spp., moderate activity against *P. melaminogenica* (1 of 2 strains) and *V. parvula*, and poor activity against *P. asaccharolytica*.

TABLE 6

Summary of in vitro MIC testing of the Active Against Anaerobic Gram-Positive and Gram-Negative Bacteria.

| Organism/ Micromyx No. | ATCC No. | The Active MIC (µg/mL) | TET MIC (µg/mL) | DOX MIC (µg/mL) | MIN MIC (µg/mL) |
|---|---|---|---|---|---|
| *Bifidobacterium bifidum* 3965 | 15696 | 1 | 1 | 0.5 | 0.25 |
| *Bifidobacterium brevi* 3967 | 15698 | 1 | 1 | 0.5 | 0.25 |
| *Bifidobacterium infantis* 3966 | 15702 | 0.5 | 1 | 0.5 | 0.25 |
| *Bifidobacterium longum* 3968 | 15707 | 4 | 2 | 1 | 1 |
| *Clostridium perfringens* 3414 | — | 16 | >16 | 16 | 16 |
| *Clostridium perfringens* 3518 | — | 16 | >16 | 16 | 8 |
| *Clostridium difficile* 3579 | — | 0.12 | 0.5 | 0.06 | 0.03 |
| *Clostridium difficile* 3584 | — | 0.12 | 0.5 | 0.06 | 0.03 |
| *Lactobacillus acidophilus* 0681 | — | 4 | 2 | 2 | 0.5 |
| *Lactobacillus casei* 1722 | 393 | 2 | 2 | 2 | 0.5 |
| *Lactobacillus plantarum* 2791 | 39268 | 2 | 2 | 2 | 0.5 |
| *Peptostreptococcus anaerobius* 3526 | — | 2 | 8 | 2 | 1 |
| *Peptostreptococcus anaerobius* 3531 | — | 4 | 16 | 4 | 2 |

TABLE 6-continued

Summary of in vitro MIC testing of the Active Against Anaerobic Gram-Positive and Gram-Negative Bacteria.

| Organism/ Micromyx No. | ATCC No. | The Active MIC (µg/mL) | TET MIC (µg/mL) | DOX MIC (µg/mL) | MIN MIC (µg/mL) |
|---|---|---|---|---|---|
| Peptostreptococcus micros 3432 | — | 0.25 | 0.25 | 0.12 | 0.06 |
| Peptostreptococcus micros 3545 | — | 1 | 1 | 0.5 | 0.25 |
| Propionibacterium acnes 1713 | — | 0.25 | 0.25 | 0.12 | 0.06 |
| Propionibacterium acnes 1286 | 11829 | 1 | 1 | 0.5 | 0.5 |
| Streptococcus constellatus 1202 | 27823 | 32 | >16 | 16 | 16 |
| Streptococcus intermedius 1203 | 27335 | 1 | 2 | 0.5 | 0.25 |
| Bacteroides fragilis 3374 | — | 0.12 | 0.5 | 0.12 | 0.03 |
| Bacteroides fragilis 3479 | — | 16 | >16 | 16 | 8 |
| Bacteroides ovatus 3503 | — | 8 | >16 | 8 | 4 |
| Bacteroides ovatus 3508 | — | 0.25 | 0.5 | 0.12 | 0.03 |
| Bacteroides thetaiotaomicron 3399 | — | 0.25 | 1 | 0.25 | 0.03 |
| Bacteroides thetaiotaomicron 3496 | — | 16 | >16 | 16 | 8 |
| Bacteroides vulgatus 3389 | — | 16 | >16 | 8 | 8 |
| Bacteroides vulgatus 3494 | — | 16 | >16 | 8 | 8 |
| Eikenella corrodens 1206 | 43278 | 1 | 0.5 | 0.12 | 0.03 |
| Fusobacterium necrophorum 3963 | 25286 | 0.25 | 0.5 | 0.5 | 0.06 |
| Fusobacterium nucleatum 3962 | 25586 | 0.25 | 0.5 | 0.5 | 0.06 |
| Porphyromonas asaccharolytica 3552 | — | 16 | >16 | 4 | 8 |
| Porphyromonas asaccharolytica 3557 | — | 8 | 16 | 2 | 4 |
| Prevotella melaninogenica 3437 | — | 32 | >16 | 16 | 16 |
| Prevotella melaninogenica 3443 | — | 4 | 8 | 1 | 1 |
| Prevotella spp. 3564 | — | 4 | 1 | 1 | 0.25 |
| Prevotella spp. 3568 | — | 2 | 4 | 1 | 0.25 |
| Veillonella parvula 1272 | 17745 | 4 | 1 | 1 | 0.5 |

"TET" is tetracycline;
"DOX" is doxycycline;
"MIN" is minocycline;
"ATCC" is American Type Culture Collection.

Antibacterial Spectrum of Activity

An assessment of the antibacterial spectrum of activity of the active was determined in several studies by in vitro MIC determination for a variety of Gram-positive and Gram-negative aerobic and anaerobic organisms. The results of these assays (summarized in Table 7) indicate that the active demonstrates activity against propionibacteria and other Gram-positive organisms with a narrower spectrum of activity than clinically-used tetracyclines. Strains resistant to tetracycline are cross-resistant to the active. The activity for each organism group is discussed in the text that follows the table.

TABLE 7

Summary of In Vitro MIC testing against propionibacteria and aerobic Gram-positive and Gram-negative organisms

| Organism [Type] (No. isolates) | Compound | MIC Range (µg/mL) | $MIC_{50}$ (µg/mL) | $MIC_{90}$ (µg/mL) |
|---|---|---|---|---|
| Propionibacteria | | | | |
| P. acnes [tetS] (13) | The Active | 0.25-4 | 0.5 | 2 |
| | Tetracycline | 0.5-4 | 0.5 | 4 |
| | Doxycycline | 0.25-1 | 0.25 | 1 |
| | Minocycline | ≤0.06->8 | 0.125 | 1 |
| P. acnes [tetR] (2) | The Active | >8->8 | | |
| | Tetracycline | >8->8 | | |
| | Doxycycline | 8-8 | | |
| | Minocycline | 2-2 | | |
| P. acnes [clinical isolates] (55) | The Active | 0.5-16 | 0.5 | 4 |
| | Tetracycline | 0.5-32 | 1 | 2 |
| | Doxycycline | 0.25-16 | 0.5 | 2 |
| | Minocycline | 0.125-8 | 0.25 | 1 |
| | Clindamycin | ≤0.06-64 | ≤0.06 | 4 |
| | Erythromycin | ≤0.06->128 | ≤0.06 | >128 |
| P. acnes [tetS] (2) | The Active | 0.25-1 | | |
| | Tetracycline | 0.25-1 | | |
| | Doxycycline | 0.12-0.5 | | |
| | Minocycline | 0.06-0.5 | | |
| | Clindamycin | 0.06-0.25 | | |
| | Metronidazole | >32->32 | | |
| | Penicillin | 0.03-0.5 | | |
| | Vancomycin | 0.5-0.5 | | |
| P. granulosum [clinical isolates] (3) | The Active | 1-1 | | |
| | Tetracycline | 1-2 | | |
| | Doxycycline | 0.5-1 | | |
| | Minocycline | 0.25-0.5 | | |
| | Clindamycin | ≤0.06-≤0.06 | | |
| | Erythromycin | ≤0.06-≤0.06 | | |

TABLE 7-continued

Summary of In Vitro MIC testing against propionibacteria and aerobic Gram-positive and Gram-negative organisms

| Organism [Type] (No. isolates) | Compound | MIC Range (µg/mL) | MIC$_{50}$ (µg/mL) | MIC$_{90}$ (µg/mL) |
|---|---|---|---|---|
| *P. avidum* [clinical isolates] (4) | The Active | 1-4 | | |
| | Tetracycline | 1-8 | | |
| | Doxycycline | 0.5-4 | | |
| | Minocycline | 0.25-2 | | |
| | Clindamycin | ≤0.06-0.5 | | |
| | Erythromycin | 0.125-0.125 | | |
| Gram-positive aerobic bacteria | | | | |
| *S. aureus* [tetS] (20) | The Active | ≤0.06-0.25 | 0.125 | 0.25 |
| | Tetracycline | ≤0.06-0.25 | 0.25 | 0.25 |
| | Doxycycline | ≤0.06-0.25 | ≤0.06 | 0.25 |
| | Minocycline | 0.125-0.5 | 0.25 | 0.5 |
| *S. aureus* [tetR] (10) | The Active | 0.125-32 | 4 | 16 |
| | Tetracycline | 2-64 | 64 | 64 |
| | Doxycycline | 1-16 | 4 | 16 |
| | Minocycline | 0.25-16 | 0.5 | 8 |
| *S. epidermidis* [MSSE] (31) | The Active | 0.12-2 | 0.25 | 2 |
| | Tetracycline | 0.12-2 | 0.25 | 2 |
| | Doxycycline | 0.06-1 | 0.12 | 1 |
| | Minocycline | 0.06-0.25 | 0.06 | 0.25 |
| | Erythromycin | 0.12->32 | 0.25 | >32 |
| | Clindamycin | ≤3.03->32 | 0.12 | >32 |
| | Oxacillin | 0.06-0.25 | 0.12 | 0.25 |
| | Vancomycin | 1-2 | 2 | 2 |
| *S. epidermidis* [MRSE] (32) | The Active | 0.25-2 | 0.5 | 2 |
| | Tetracycline | 0.25->32 | 1 | 2 |
| | Doxycycline | 0.12-8 | 0.5 | 1 |
| | Minocycline | 0.06-0.5 | 0.12 | 0.25 |
| | Erythromycin | 0.12->32 | >32 | >32 |
| | Clindamycin | 0.06->32 | >32 | >32 |
| | Oxacillin | 0.5->32 | 32 | >32 |
| | Vancomycin | 1-2 | 2 | 2 |
| *S. pneumoniae* [tetS] (5) | The Active | ≤0.06-0.125 | | |
| | Tetracycline | ≤0.06-0.25 | | |
| | Doxycycline | ≤0.06-0.125 | | |
| | Minocycline | 0.25-0.25 | | |
| *S. pneumoniae* [tetR] (5) | The Active | 4-32 | | |
| | Tetracycline | 32-64 | | |
| | Doxycycline | 4-4 | | |
| | Minocycline | 8-16 | | |
| *S. pneumoniae* [PSSP] (32) | The Active | ≤3.03-32 | 0.12 | 0.25 |
| | Tetracycline | 0.06->32 | 0.12 | 0.25 |
| | Doxycycline | 0.03->16 | 0.06 | 0.12 |
| | Minocycline | ≤0.015->16 | 0.06 | 0.12 |
| | Erythromycin | ≤0.015->16 | 0.03 | 2 |
| | Clindamycin | ≤0.015->16 | 0.03 | 0.06 |
| | Penicillin | ≤0.015-0.12 | ≤0.015 | 0.06 |
| | Vancomycin | 0.06-0.25 | 0.25 | 0.25 |
| *S. pyogenes* (32) | The Active | 0.12-16 | 0.12 | 8 |
| | Tetracycline | 0.12-32 | 0.12 | 32 |
| | Doxycycline | 0.06-8 | 0.12 | 4 |
| | Minocycline | 0.03-8 | 0.06 | 8 |
| | Erythromycin | 0.03->16 | 0.06 | 0.06 |
| | Clindamycin | 0.03->16 | 0.03 | 0.06 |
| | Penicillin | ≤0.015-0.25 | ≤0.015 | ≤0.015 |
| | Vancomycin | 0.25-0.5 | 0.25 | 0.25 |
| *S. pyogenes* [tetS] (5) | The Active | ≤0.06-0.25 | | |
| | Tetracycline | ≤0.06-0.125 | | |
| | Doxycycline | ≤0.06-0.125 | | |
| | Minocycline | 0.25-0.5 | | |
| *S. pyogenes* [tetR] (5) | The Active | 4-16 | | |
| | Tetracycline | 32-64 | | |
| | Doxycycline | 4-8 | | |
| | Minocycline | 4-8 | | |
| *S. agalactiae* (31) | The Active | 0.12-32 | 16 | 16 |
| | Tetracycline | 0.12->32 | 32 | >32 |
| | Doxycycline | 0.06-16 | 8 | 16 |
| | Minocycline | 0.03-16 | 16 | 16 |
| | Erythromycin | 0.03->16 | 0.06 | >16 |
| | Clindamycin | 0.03->16 | 0.06 | >16 |
| | Penicillin | ≤0.015-2 | 0.03 | 1 |
| | Vancomycin | 0.25-2 | 0.5 | 0.5 |

TABLE 7-continued

Summary of In Vitro MIC testing against propionibacteria and aerobic Gram-positive and Gram-negative organisms

| Organism [Type] (No. isolates) | Compound | MIC Range (µg/mL) | $MIC_{50}$ (µg/mL) | $MIC_{90}$ (µg/mL) |
|---|---|---|---|---|
| S. agalactiae [tetS] (3) | The Active | 0.125-0.25 | | |
| | Tetracycline | 0.25-0.25 | | |
| | Doxycycline | 0.25-0.25 | | |
| | Minocycline | 0.5-0.5 | | |
| S. agalactiae [tetR] (7) | The Active | 16-32 | | |
| | Tetracycline | 16-64 | | |
| | Doxycycline | 8-16 | | |
| | Minocycline | 8-16 | | |
| S. haemolyticus (33) | The Active | 0.12-2 | 0.12 | 2 |
| | Tetracycline | 0.12->32 | 1 | >32 |
| | Doxycycline | 0.06-16 | 0.5 | 16 |
| | Minocycline | ≤0.03-0.5 | 0.06 | 0.5 |
| | Erythromycin | 0.12->32 | >32 | >32 |
| | Clindamycin | 0.06->32 | 0.12 | 1 |
| | Oxacillin | 0.06->32 | 0.25 | >32 |
| | Vancomycin | 0.5-2 | 1 | 1 |
| Streptococcus spp. [Group C] (30) | The Active | 0.12-16 | 0.25 | 16 |
| | Tetracycline | 0.12->32 | 0.25 | 32 |
| | Doxycycline | 0.06-16 | 0.12 | 8 |
| | Minocycline | 0.03-8 | 0.06 | 8 |
| | Erythromycin | ≤0.015->16 | 0.06 | 4 |
| | Clindamycin | ≤0.015->16 | 0.06 | 0.12 |
| | Penicillin | ≤0.015-0.03 | ≤0.015 | ≤0.015 |
| | Vancomycin | 0.25-1 | 0.25 | 0.5 |
| E. faecalis [tetS] (4) | The Active | ≤0.06-≤0.06 | | |
| | Tetracycline | 0.25-0.5 | | |
| | Doxycycline | ≤0.06-0.125 | | |
| | Minocycline | 0.25-0.5 | | |
| E. faecalis [tetR] (6) | The Active | 8-32 | | |
| | Tetracycline | 32-64 | | |
| | Doxycycline | 2-16 | | |
| | Minocycline | 4-16 | | |
| E. faecalis [VSE] (31) | The Active | 0.25-32 | 32 | 32 |
| | Tetracycline | 0.25->64 | 32 | 64 |
| | Doxycycline | 0.12-16 | 8 | 8 |
| | Minocycline | 0.06-16 | 8 | 16 |
| | Erythromycin | 0.25->32 | >32 | >32 |
| | Clindamycin | 4->32 | >32 | >32 |
| | Ampicillin | 0.5-8 | 1 | 1 |
| | Vancomycin | 0.5-4 | 1 | 2 |
| E. faecium [tetS] (4) | The Active | ≤0.06-≤0.06 | | |
| | Tetracycline | 0.125-0.25 | | |
| | Doxycycline | ≤0.06-≤0.06 | | |
| | Minocycline | 0.25-0.5 | | |
| E. faecium [tetR] (6) | The Active | 8-32 | | |
| | Tetracycline | 32-64 | | |
| | Doxycycline | 4-16 | | |
| | Minocycline | 2-32 | | |
| E. faecium [VSE] (32) | The Active | 0.12-32 | 0.5 | 32 |
| | Tetracycline | 0.12->64 | 1 | >64 |
| | Doxycycline | 0.06-32 | 0.5 | 16 |
| | Minocycline | ≤0.03-16 | 0.12 | 16 |
| | Erythromycin | 0.06->32 | >32 | >32 |
| | Clindamycin | 0.12->32 | >32 | >32 |
| | Ampicillin | 0.12->64 | 64 | >64 |
| | Vancomycin | 0.25-2 | 1 | 1 |
| E. faecium [VRE] (30) | The Active | 0.12-32 | 2 | 32 |
| | Tetracycline | 0.12->64 | 2 | >64 |
| | Doxycycline | 0.06-16 | 1 | 8 |
| | Minocycline | ≤0.03-16 | 0.25 | 16 |
| | Erythromycin | 0.12->32 | >32 | >32 |
| | Clindamycin | 0.06->32 | >32 | >32 |
| | Ampicillin | 8->64 | >64 | >64 |
| | Vancomycin | >64 | >64 | >64 |
| Gram-negative aerobic bacteria | | | | |
| E. coli [tetS] (7) | The Active | 4-32 | | |
| | Tetracycline | 1-4 | | |
| | Doxycycline | 0.5-4 | | |
| | Minocycline | 0.5-4 | | |
| E. coli [tetR] | The Active | >64->64 | | |
| | Tetracycline | >64->64 | | |

TABLE 7-continued

Summary of In Vitro MIC testing against propionibacteria and aerobic Gram-positive and Gram-negative organisms

| Organism [Type] (No. isolates) | Compound | MIC Range (μg/mL) | MIC$_{50}$ (μg/mL) | MIC$_{90}$ (μg/mL) |
|---|---|---|---|---|
| (3) | Doxycycline | 64-64 | | |
| | Minocycline | 8-16 | | |
| E. coli (33) | The Active | 2->64 | 16 | >64 |
| | Tetracycline | 1->64 | 2 | >64 |
| | Doxycycline | 0.5->32 | 2 | 32 |
| | Minocycline | 0.25->32 | 1 | 8 |
| | Ampicillin | 1->64 | >64 | >64 |
| | Ciprofloxacin | 0.008->2 | 0.015 | >2 |
| | Cephalothin | 2->64 | 32 | >64 |
| | Tmp/Sxt | ≤0.06/1.19->64/1216 | 0.25/4.75 | >64/1216 |
| K. pneumoniae [tetS] (7) | The Active | 16-64 | | |
| | Tetracycline | 0.5-4 | | |
| | Doxycycline | 0.5-8 | | |
| | Minocycline | 1-16 | | |
| K. pneumoniae [tetR] (5) | The Active | >64->64 | | |
| | Tetracycline | 8->64 | | |
| | Doxycycline | 16-64 | | |
| | Minocycline | 16->64 | | |
| K. pneumoniae (31) | The Active | 16->64 | >64 | >64 |
| | Tetracycline | 1->64 | 8 | >64 |
| | Doxycycline | 1->32 | 8 | >32 |
| | Minocycline | 1->32 | 4 | >32 |
| | Ampicillin | >64 | >64 | >64 |
| | Ciprofloxacin | 0.03->2 | >2 | >2 |
| | Cephalothin | >64 | >64 | >64 |
| | Tmp/Sxt | 0.12/2.38->64/1216 | >64/1216 | >64/1216 |
| E. cloacae (30) | The Active | 0.25->64 | 32 | >64 |
| | Tetracycline | 0.5->64 | 2 | >64 |
| | Doxycycline | 0.06->32 | 2 | 32 |
| | Minocycline | ≤0.03->32 | 1 | 16 |
| | Ampicillin | 4->64 | 64 | >64 |
| | Ciprofloxacin | 0.008->2 | 0.25 | >2 |
| | Cephalothin | 2->64 | >64 | >64 |
| | Tmp/Sxt | ≤0.06/1.19->64/1216 | 0.25/4.75 | >64/1216 |
| P. mirabilis (30) | The Active | >64 | >64 | >64 |
| | Tetracycline | 16->64 | 32 | 64 |
| | Doxycycline | 32->32 | >32 | >32 |
| | Minocycline | 8->32 | 16 | >32 |
| | Ampicillin | 0.5->64 | 4 | >64 |
| | Ciprofloxacin | 0.015->2 | >2 | >2 |
| | Cephalothin | 2->64 | 8 | >64 |
| | Tmp/Sxt | ≤0.06/1.19->64/1216 | 2/38 | >64/1216 |
| P. aeruginosa (11) | The Active | 32->64 | >64 | >64 |
| | Tetracycline | 4->64 | 64 | 64 |
| | Doxycycline | 4->32 | >32 | >32 |
| | Minocycline | 8->32 | >32 | >32 |
| | Ampicillin | >64 | >64 | >64 |
| | Ciprofloxacin | 0.12->2 | >2 | >2 |
| | Cephalothin | >64 | >64 | >64 |
| | Tmp/Sxt | 2/38->64/1216 | 16/304 | >64/1216 |
| Salmonella spp. (35) | The Active | 8->64 | 16 | >64 |
| | Tetracycline | 1->64 | 2 | >64 |
| | Doxycycline | 2->32 | 2 | 32 |
| | Minocycline | 1->32 | 2 | 8 |
| | Ampicillin | 0.5->64 | 1 | >64 |
| | Ciprofloxacin | 0.015-0.25 | 0.015 | 0.03 |
| | Cephalothin | 1->64 | 2 | 16 |
| | Tmp/Sxt | ≤0.06/1.19->64/1216 | ≤0.06/1.19->64/1216 | 0.12/2.38 |

Abbreviations used in Table 7:
tetS, tetracycline sensitive;
tetR, tetracycline resistant;
VSE, vancomycin-susceptible *Enterococcus*;
VRE, vancomycin-resistant *Enterococcus*;
MSSE, methicillin-susceptible *Staphylococcus epidermidis*;
MRSE, methicillin-resistant *Staphylococcus epidermidis*;
PSSP, penicillin-susceptible *Streptococcus pneumoniae*;
MIC, minimum inhibitory concentration;
MIC$_{50}$, MIC at which 50% of isolates are inhibited;
MIC$_{90}$, MIC at which 90% of the isolates are inhibited.

In Vitro Antibacterial Activity of the Active Against Propionibacteria

The in vitro antimicrobial activity of the active against the acne vulgaris pathogen *P. acnes* was assessed using the Clinical and Laboratory Standards Institute (CLSI)-approved agar dilution method for anaerobes. Susceptibility testing was performed by measuring the MIC against a screening panel of *P. acnes* including several macrolide-resistant strains. The values determined for the active were compared with similar members of the tetracycline class of antibiotics, including the clinically-used acne therapeutics, doxycycline and minocycline (Table 7). Against a panel of 13 tetracycline-sensitive *P. acnes*, the active demonstrated MICs comparable to doxycycline and minocycline.

In an expanded study, the active was tested against 62 recent clinical isolates of propionibacteria along with several tetracycline comparators (Table 7). Against 55 strains of *P. acnes* isolated within the past 7 years, including 26 isolates obtained within the past 3 years, the active demonstrated activity similar to that of doxycycline.

In Vitro Antimicrobial Activity of the Active against Staphylococci

Thirty strains of *S. aureus* were tested against the active (Table 7) and conventional tetracyclines (tetracycline, doxycycline, and minocycline). Typed strains with known resistance mechanisms, ribosomal protection and active efflux, were included. Activity was variable and compared to doxycycline and minocycline.

In Vitro Antimicrobial Activity of the Active Against Streptococci

Thirty strains of streptococci (10 each *S. pyogenes, S. agalactiae*, and *S. pneumoniae*) were tested against the active and conventional tetracyclines (tetracycline, doxycycline, and minocycline). Typed strains with known resistance to tetracycline and minocycline, characteristic of ribosomal protection mediated by tetM or tetO, were included. Similar to staphylococci, MIC ranges and $MIC_{90}$ values (Table 7) were closest to minocycline and doxycycline. The active showed good activity against susceptible strains of *S. pyogenes*, with MICs comparable to doxycycline and minocycline.

The active demonstrated a bimodal distribution of MIC values for *S. agalactiae* with 7 strains inhibited at 0.25 µg/mL or less, and the remainder of the isolates requiring 16-32 µg/mL for inhibition. The elevated MIC values tracked with resistance to tetracycline. The $MIC_{50}$ and $MIC_{90}$ values for the active were similar to those of doxycycline and minocycline but less than that of tetracycline.

The active demonstrated potent activity against PSSP with all but 3 strains inhibited at 0.25 µg/mL or less. The elevated MIC values tracked with resistance to tetracycline. The activity was similar to that of tetracycline, doxycycline and minocycline.

The active demonstrated potent activity against *S. pyogenes* with all but 6 strains inhibited at 0.25 µg/mL or less. Elevated MICs (≥4 µg/mL) were observed for 5 strains which tracked with resistance to tetracycline. The $MIC_{90}$ value for the active was similar to those of doxycycline and minocycline but less than that of tetracycline.

The active demonstrated a bimodal distribution of MIC values for Group C streptococci with 19 strains inhibited at 0.25 µg/mL or less, and the remainder of the isolates requiring 4-16 µg/mL for inhibition. The elevated MIC values tracked with resistance to tetracycline. The $MIC_{50}$ and $MIC_{90}$ values for the active were similar to those of tetracycline but higher than those of doxycycline and minocycline.

In Vitro Antimicrobial Activity of the Active Against Enterococci

Twenty enterococcal strains (10 each *E. faecalis* and *E. faecium*) were tested against the active and conventional tetracyclines (tetracycline, doxycycline, and minocycline), including 11 well characterized tetracycline-resistant strains (Table 7). Unlike the staphylococci, the active was not active against any tetracycline-resistant strains by efflux (mediated by tetK or tetL) or by ribosomal protection (tetM or tetO). The active did show activity against tetracycline-susceptible strains of *E. faecalis* and *E. faecium* which was comparable to that of doxycycline.

The active demonstrated a bimodal distribution of MIC values for vancomycin-susceptible *E. faecalis* with 8 strains inhibited at 0.5 µg/mL or less, and the remainder of the isolates requiring 16-32 µg/mL for inhibition. The elevated MIC values tracked with resistance to tetracycline. The $MIC_{50}$ and $MIC_{90}$ values for the active were similar to those of tetracycline and greater than those of doxycycline and minocycline.

The active also demonstrated bimodal distribution of MIC values for vancomycin-susceptible *E. faecium* with 17 strains inhibited at 0.5 µg/mL or less, and the remainder of the isolates requiring 16-32 µg/mL for inhibition. The elevated MIC values tracked with resistance to tetracycline. The $MIC_{50}$ and $MIC_{90}$ values for the active were similar to those of doxycycline and minocycline with an $MIC_{90}$ value lower than that of tetracycline.

The active demonstrated a broad range of MIC values for vancomycin-resistant *E. faecium*. The elevated MIC values tracked with resistance to tetracycline. The $MIC_{50}$ value for the active was similar to that of tetracycline and doxycycline and 8-fold higher than that of minocycline. The $MIC_{90}$ value for the active was lower than that of tetracycline and greater than that of doxycycline and minocycline. A high percentage of strains were resistant to the rest of the test agents.

In Vitro Antimicrobial Activity Against Gram-negative Bacteria

Against 7 tetracycline-sensitive strains of *E. coli*, the active was less active in vitro than doxycycline and minocycline (Table 7). Even less activity for the active was observed against tetracycline-sensitive strains of *K. pneumoniae*. In contrast, doxycycline and minocycline demonstrated greater activity against these organisms than the active. As expected, no activity for the active was observed against 6 tetracycline resistant strains demonstrating active efflux mediated by tetB or tetD.

The active had generally poor activity against *E. cloacae* though a small number of strains (7 of 30) were inhibited at 1 µg/mL or less. The $MIC_{50}$ value was 16- to 32-fold higher than those of the other tetracyclines. The $MIC_{90}$ value for the active was the same as tetracycline and higher than that of doxycycline or minocycline.

The active was the least active of the tetracyclines against *E. coli* with $MIC_{50}$ and $MIC_{90}$ values of 16 and >64 µg/mL, respectively. The active was the least active of the tetracyclines against *K. pneumoniae*. The active had generally poor activity against *Salmonella* spp. and was the least active of the tetracyclines.

Mechanism of Action

For the studies below, samples were prepared with bis hydrochloride salt, and the data is expressed based on the free base ("the active"). The mechanism of action of the Crystalline Mono Hydrochloride Salt was determined by two different approaches via study of the active, as described below.

In the first approach, Antibacterial Mechanism of Action: In Vitro Inhibition of Bacterial Transcription and Translation, the ability of the active to inhibit bacterial protein synthesis was assessed using an in vitro cell-free bacterial transcription and translation assay (commercially-available from Promega Corporation, Madison, Wis.) (Beckler, G., Promega Notes 31 (1991) pp. 3-6). The active inhibited the synthesis of reporter protein with an $IC_{50}$ of 8.3±0.18 µM. This value was comparable to the $IC_{50}$ values determined for the comparator tetracyclines, doxycycline and minocycline ($IC_{50}$ values of 4.7±0.48 and 2.4±0.22 µM, respectively). These results provide evidence that the active functions as a classical tetracycline by inhibiting bacterial protein synthesis.

In the second approach, Antibacterial Mechanism of Action. Inhibition of Macromolecular Synthesis in *Staphylococcus aureus*, the ability of the active to target bacterial protein synthesis was further confirmed in a whole-cell assay of macromolecular synthesis in the Gram-positive organism, *S. aureus*. The active inhibited, in a dose-dependent manner, the incorporation of [$^3$H]-leucine into proteins of the growing organism within the concentration range of 0.25-8 fold the MIC (0.063-2 µg/mL). A maximum inhibition of 80% was observed at 8-fold the MIC which was comparable to the values obtained for the tetracycline comparators doxycycline and minocycline. In contrast, the active at 8-fold the MIC demonstrated less than 20% inhibition for the synthesis of cell wall, DNA, RNA and lipid components of the test bacteria. The results of this study indicate that the active acts as a selective inhibitor of bacterial protein synthesis at concentrations comparable to known tetracyclines.

The in vitro susceptibility studies described above included tetracycline-resistant strains with characterized tetracycline resistance genes. Strains were selected that harbored the most common tetracycline resistance genes: efflux (tetK, tet38, tetL, tetS, tetB, and tetD), ribosomal protection (tetM and tetO), as well as *P. acnes* resistant by rRNA point mutation. The MIC values for these selected strains demonstrated a degree of cross-resistance between the active and other tetracyclines, as shown in Table 8. The presence of a tetracycline resistance gene increased the MIC of the active relative to susceptible strains (with the exception of tetK in *S. aureus*), with MIC values similar to those of doxycycline and/or minocycline, but generally lower than those of tetracycline.

TABLE 8

Activity of the Active Against Bacterial Strains with Characterized Tetracycline Resistance Mechanisms.

| Organism | Strain PBS # | Mech./ Genotype | The Active MIC (µg/mL) | Doxycycline MIC (µg/mL) | Minocycline MIC (µg/mL) |
| --- | --- | --- | --- | --- | --- |
| P. acnes | 1073 | 16S rRNA point mutation | >8 | 8 | 2 |
| S. aureus | 1739 | tet38 | 4 | 2 | 0.5 |
| E. coli | 669 | tetB | >64 | 64 | 16 |
| K. pneumoniae | 266 | tetD | >64 | 64 | 64 |
| S. aureus | 1309 | tetK | 0.5 | 2 | 0.5 |
| E. faecium | 1323 | tetK | 8 | 4 | 2 |
| E. faecalis | 274 | tetL | 32 | 16 | 16 |
| S. aureus | 1310 | tetM | 8 | 16 | 4 |
| S. pyogenes | 792 | tetM | 4 | 4 | 4 |
| S. agalactiae | 897 | tetM | 16 | 8 | 16 |
| S. pneumoniae | 511 | tetM | 4 | 4 | 8 |
| E. faecalis | 276 | tetM | 16 | 8 | 16 |
| E. faecium | 965 | tetM | 8 | 4 | 8 |
| S. pyogenes | 330 | tetO | 16 | 8 | 8 |
| S. agalactiae | 316 | tetO | 32 | 8 | 16 |
| E. faecium | 1324 | tetO | 16 | 4 | 2 |
| E. faecalis | 949 | tetS | 8 | 2 | 4 |

Animal Models of Infection

For the studies below, samples were prepared with bis hydrochloride salt, and the data is expressed based on the free base ("the active"). In vivo efficacy studies were conducted with the active in three distinct animal infection models and one inflammation model. By possessing comparable activity to the active, the studies show: 1) anti-infective efficacy of the Crystalline Mono Hydrochloride Salt compared to other commercially available tetracycline acne medications (doxycycline and minocycline) against representative Gram-positive pathogens with similar in vitro susceptibility as *P. acnes*; and 2) the anti-inflammatory activity of Crystalline Mono Hydrochloride Salt.

The comparators were dosed at a concentration of 10 mg/mL in a vehicle of sterile water and adjusted for percent of their active moiety. All studies, except for the thigh wound and rat footpad edema studies, were conducted in CD-1 male mice. The thigh wound model was conducted using CD-1 female mice and the rat footpad edema studies were conducted with Sprague-Dawley male rats.

Table 9 presents the data collected from the following three studies, which evaluated the efficacy of the active.

The first study evaluated the active in an *S. aureus* Systemic Intraperitoneal Challenge (IPC) Model. The objective was to assess the in vivo activity of the active against a Gram-positive organism in an acute infectious model compared to commercially-available tetracycline treatments for acne vulgaris. Bacterial cultures were prepared by growing tetracycline-sensitive *S. aureus* RN450-1 overnight, then diluting with sterile phosphate-buffered saline (PBS). For each experiment, a total of 30 mice were infected by injection into the intraperitoneal cavity with 500 nl of 7.5×10' CFU in 5% sterile bacteriological mucin. Four to five treatment groups of 5 mice each were treated with a single injection of the active, doxycycline, and/or minocycline at doses ranging from 0.01-0.5 mg/kg in sterile water. The doses were administered subcutaneously (SC) at 1 hour post infection. An additional infected group of 5 mice was included as a negative control (untreated) group. For all studies but one, a positive control group(s) was included (e.g., doxycycline, minocycline, or ciprofloxacin). Mice were monitored for survival for up to 7 days. Efficacy was determined by calculating the $PD_{50}$ at 48 hours post infection. $PD_{50}$ (protective dose, 50%) is the dose required to achieve 50% survival. The $PD_{50}$ values reported are a mean of 2-3 independent experiments for each drug tested.

The active displayed potent activity against *S. aureus* RN450-1 resulting in a $PD_{50}$ of 0.25 mg/kg and demonstrated activity similar to doxycycline against a representative Gram-positive pathogen.

The second study, Efficacy of the Active in a *S. aureus* Thigh Wound Infection Model, looked at the activity of the active against a representative Gram-positive infection in a tissue-based infection model. The efficacy of the active was studied against *S. aureus* RN450-1 in a thigh wound model of immunocompromised mice. A total of 40 mice (n=4-8 mice per group) were rendered neutropenic by cyclophosphamide treatment four days before (150 mg/kg) and one day before (100 mg/kg) infection. Bacterial cultures were prepared by growing *S. aureus* RN450-1 overnight and diluting with sterile PBS. An injection of 100 µL of ~1×10$^6$ CFU/mL in sterile PBS was injected into the thigh. Four groups of mice for each drug received doses of 0.33, 1, 3, or 9 mg/kg intravenously at 2 and 6 hours post infection. An additional group of untreated mice served as a negative control group. At 24 hours post infection, the thighs were collected aseptically, homogenized, and plated to enumerate bacterial load per thigh. Data are reported as $ED_{50}$ values. $ED_{50}$ (effective dose, 50%) is the dose required to achieve a 2 $log_{10}$ reduction in bacterial burden (colony forming units [CFU]/whole organ) in the target organ compared to untreated controls.

As shown in Table 9, the active demonstrated efficacy equivalent to doxycycline, a commonly used treatments for acne vulgaris, in the S. aureus thigh wound model.

The third study, Efficacy of the Active in an Acute S. pneumoniae Respiratory Tract Infection (RTI) Model, demonstrated activity of the active in an additional tissue-based infection model compared to doxycycline. The active and doxycycline were tested independently against an S. pneumoniae-induced acute pneumonia in immunocompromised mice. In each experiment, 35 mice were rendered neutropenic by an intraperitoneal (IP) injection of cyclophosphamide four days before (150 mg/kg) and one day before (100 mg/kg) infection. Tetracycline-sensitive S. pneumoniae PBS1339 was grown on plates overnight, colonies collected, and resuspended in sterile PBS. Mice were infected intra-nasally with 50 μL of this bacterial suspension containing ~6×10$^6$ CFU/mouse. At 2 hours post infection, 4 to 5 groups of 5 mice each were treated with a single intravenous (IV) dose of the active or doxycycline at 5 (the active only), 10, 20, 40, or 80 mg/kg dissolved in sterile water. Each study also had an untreated control group and a group that received a positive control compound (e.g., vancomycin at 20 mg/kg IV). Efficacy was determined by calculating the $PD_{50}$ at 72 hours post infection.

A single IV dose of the active exhibited activity in a neutropenic, lethal S. pneumoniae RTI model at a $PD_{50}$ of 4.66 mg/kg (as shown in Table 9). This dose was slightly lower than the 7.18 mg/kg dose required to achieve the $PD_{50}$ for doxycycline. The active demonstrated activity in this additional tissue-based infection model that was comparable to, or slightly better than, that of doxycycline.

TABLE 9

Efficacy Summary of the Active and Comparators in Murine Infection Models.

| Compound | S. aureus RN450-1 IPC $PD_{50}$ (mg/kg) | S. aureus RN450-1 Thigh $ED_{50}$ (mg/kg) | S. pneumoniae PBS1339 RTI $PD_{50}$ (mg/kg) |
|---|---|---|---|
| The Active | 0.25 | 8.23 | 4.66 |
| Doxycycline | 0.30 | 8.31 | 7.18 |
| Minocycline | 0.03 | — | — |

The study, In Vivo Efficacy of the Active in an Inflammation Model of Rat Carrageenan-Induced Footpad Edema, was conducted to evaluate the anti-inflammatory properties of the active compared to minocycline and doxycycline. Groups of 3-8 rats were injected IP with the active, doxycycline, minocycline, and/or saline control at 5 minutes preceding an injection of the inflammatory carrageenan solution (1 mg/100 μL) in the hind paw. Each study also had a saline treated control group (3-8 rats/group). The active was tested at 5, 10, 25, 50, 75, 100, or 150 mg/kg. Minocycline was tested at 25, 50, 75, or 100 mg/kg and doxycycline was tested at 75 and 100 mg/kg. Immediately following the carrageenan injection and 3 hours post-injection, the hind paw volume was measured with a digital water plethysmometer. Results were calculated as a percent change in paw volume over the 3 hours, divided by the baseline paw volume, and then adjusted for the mean percent inflammation in the untreated controls, and are presented in Table 10. The active, doxycycline, and minocycline all demonstrated anti-inflammatory activity at all doses tested. The active exhibited anti-inflammatory activity in a standard animal model of inflammation comparable to other commercially-available tetracyclines commonly used for the treatment of acne vulgaris.

TABLE 10

Mean inhibition of Inflammation by the Active in a Carrageenan-Induced Rat Footpad Edema Model.
Mean Percent Inflammation Compared to Untreated Controls

| Compound | 150 mg/kg | 100 mg/kg | 75 mg/kg | 50 mg/kg | 25 mg/kg | 10 mg/kg | 5 mg/kg | 1 mg/kg |
|---|---|---|---|---|---|---|---|---|
| The Active | 26 | 53 | 56 | 52 | 59 | 65 | 78 | 103 |
| Doxycycline | — | 36 | 68 | — | — | — | — | — |
| Minocycline | — | 21 | 54 | 33 | 47 | — | — | — |

Numerous alterations, modifications, and variations of the preferred embodiments disclosed herein will be apparent to those skilled in the art, and they are all anticipated and contemplated to be within the spirit and scope of the claimed invention. For example, although specific embodiments have been described in detail, those with skill in the art will understand that the preceding embodiments and variations can be modified to incorporate various types of substitute, additional or alternative materials. Accordingly, even though only few variations of the present invention are described herein, it is to be understood that the practice of such additional modifications and variations and the equivalents thereof, are within the spirit and scope of the invention as defined in the following claims. All patent applications, patents, and other publications cited herein are incorporated by reference in their entirety.

What is claimed is:

1. A crystalline salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, wherein the salt is selected from a group consisting of mono hydrochloride, mono mesylate and mono sulfate, and wherein the crystalline salt has a crystal-like internal structural arrangement.

2. The crystalline salt of claim 1, wherein the salt is substantially pure.

3. The crystalline salt of claim 1, wherein the salt is mono hydrochloride.

4. The crystalline salt of claim 3, having an XRPD pattern substantially as illustrated in FIG. 1 after synthesis of the crystalline salt.

5. The crystalline salt of claim 3, having at least three characteristic peaks at diffraction angle 2-theta degrees appearing at about 13.4, about 20.5 and about 23.3, as measured by XRPD.

6. The crystalline salt of claim 3, having a DSC curve substantially as illustrated in FIG. 2 after synthesis of the crystalline salt.

7. The crystalline salt of claim 3, having a TGA curve substantially as illustrated in FIG. 3 after synthesis of the crystalline salt.

8. The crystalline salt of claim 3, wherein the salt has a β-isomer content at 0 days of about 0.1% peak area to about 7.0% peak area, as measured by HPLC.

9. The crystalline salt of claim 1, wherein the salt is mono mesylate.

10. The crystalline salt of claim 9, having an XRPD pattern substantially as illustrated in FIG. 4 after synthesis of the crystalline salt.

11. The crystalline salt of claim 9, having at least three characteristic peaks at diffraction angle 2-theta degrees appearing at about 9, about 15 and about 23.8, as measured by XRPD.

12. The crystalline salt of claim 9, having a DSC curve substantially as illustrated in FIG. 5 after synthesis of the crystalline salt.

13. The crystalline salt of claim 9, having a TGA curve substantially as illustrated in FIG. 6 after synthesis of the crystalline salt.

14. The crystalline salt of claim 9, wherein the salt has a β-isomer content at 0 days of about 2.0% peak area to about 10.0% peak area, as measured by HPLC.

15. The crystalline salt of claim 1, wherein the salt is mono sulfate.

16. The crystalline salt of claim 15, having an XRPD pattern substantially as illustrated in FIG. 7 after synthesis of the crystalline salt.

17. The crystalline salt of claim 15, having at least three characteristic peaks at diffraction angle 2-theta degrees appearing at about 15, about 17.8 and about 23.5, as measured by XRPD.

18. The crystalline salt of claim 15, having a DSC curve substantially as illustrated in FIG. 8 after synthesis of the crystalline salt.

19. The crystalline salt of claim 15, having a TGA curve substantially as illustrated in FIG. 9 after synthesis of the crystalline salt.

20. The crystalline salt of claim 15, wherein the salt has a β-isomer content at 0 days of about 3.0% peak area to about 26.0% peak area, as measured by HPLC.

21. A pharmaceutical composition comprising the crystalline salt of claim 1 and a pharmaceutically acceptable excipient.

22. The pharmaceutical composition of claim 21, wherein the salt is mono hydrochloride.

23. The pharmaceutical composition of claim 21, wherein the salt is mono mesylate.

24. The pharmaceutical composition of claim 21, wherein the salt is mono sulfate.

25. A method for treating acne comprising administering to a subject a therapeutically effective amount of the crystalline salt of claim 1.

26. The method of claim 25, wherein the salt is mono hydrochloride.

27. The method of claim 25, wherein the salt is mono mesylate.

28. The method of claim 25, wherein the salt is mono sulfate.

29. A method for treating rosacea comprising administering to a subject a therapeutically effective amount of the crystalline salt of claim 1.

30. The method of claim 29, wherein the salt is mono hydrochloride.

31. The method of claim 29, wherein the salt is mono mesylate.

32. The method of claim 29, wherein the salt is mono sulfate.

33. A method for treating a gram positive bacterial infection, wherein the gram positive bacteria is selected from the group consisting of *Propionibacterium acnes*, *Staphylococcus aureus*, *Streptococcus pneumonia*, *Streptococcus pyogenes*, and *Clostridium difficile*, comprising administering to a subject a therapeutically effective amount of the crystalline salt of claim 1.

34. The method of claim 33, wherein the salt is mono hydrochloride.

35. The method of claim 33, wherein the salt is mono mesylate.

36. The method of claim 33, wherein the salt is mono sulfate.

37. A crystalline salt of (4S,4aS,5aR,12aS)-4-dimethylamino-3,10,12,12a-tetrahydroxy-7-[(methoxy(methyl)amino)-methyl]-1,11-dioxo-1,4,4a,5,5a,6,11,12a-octahydro-naphthacene-2-carboxylic acid amide, wherein the salt is selected from a group consisting of mono hydrochloride, mono mesylate and mono sulfate, and wherein the crystalline salt is substantially free of an amorphous salt.

38. The crystalline salt of claim 37, wherein the salt is substantially pure.

39. The crystalline salt of claim 37, wherein the salt is mono hydrochloride.

40. The crystalline salt of claim 39, having an XRPD pattern substantially as illustrated in FIG. 1 after synthesis of the crystalline salt.

41. The crystalline salt of claim 39, having at least three characteristic peaks at diffraction angle 2-theta degrees appearing at about 13.4, about 20.5 and about 23.3, as measured by XRPD.

42. The crystalline salt of claim 39, having a DSC curve substantially as illustrated in FIG. 2 after synthesis of the crystalline salt.

43. The crystalline salt of claim 39, having a TGA curve substantially as illustrated in FIG. 3 after synthesis of the crystalline salt.

44. The crystalline salt of claim 39, wherein the salt has a β-isomer content at 0 days of about 0.1% peak area to about 7.0% peak area, as measured by HPLC.

45. The crystalline salt of claim 37, wherein the salt is mono mesylate.

46. The crystalline salt of claim 45, having an XRPD pattern substantially as illustrated in FIG. 4 after synthesis of the crystalline salt.

47. The crystalline salt of claim 45, having at least three characteristic peaks at diffraction angle 2-theta degrees appearing at about 48, about 15 and about 23.8, as measured by XRPD.

48. The crystalline salt of claim 45, having a DSC curve substantially as illustrated in FIG. 5 after synthesis of the crystalline salt.

49. The crystalline salt of claim 45, having a TGA curve substantially as illustrated in FIG. 6 after synthesis of the crystalline salt.

50. The crystalline salt of claim 45, wherein the salt has a β-isomer content at 0 days of about 2.0% peak area to about 10.0% peak area, as measured by HPLC.

51. The crystalline salt of claim 37, wherein the salt is mono sulfate.

52. The crystalline salt of claim 51, having an XRPD pattern substantially as illustrated in FIG. 7 after synthesis of the crystalline salt.

53. The crystalline salt of claim 51, having at least three characteristic peaks at diffraction angle 2-theta degrees appearing at about 15, about 17.8 and about 23.5, as measured by XRPD.

54. The crystalline salt of claim 51, having a DSC curve substantially as illustrated in FIG. 8 after synthesis of the crystalline salt.

55. The crystalline salt of claim 51, having a TGA curve substantially as illustrated in FIG. 9 after synthesis of the crystalline salt.

56. The crystalline salt of claim 51, wherein the salt has a β-isomer content at 0 days of about 3.0% peak area to about 26.0% peak area, as measured by HPLC.

57. A pharmaceutical composition comprising the crystalline salt of claim 37 and a pharmaceutically acceptable excipient.

58. The pharmaceutical composition of claim 57, wherein the salt is mono hydrochloride.

59. The pharmaceutical composition of claim 57, wherein the salt is mono mesylate.

60. The pharmaceutical composition of claim 57, wherein the salt is mono sulfate.

61. A method for treating acne comprising administering to a subject a therapeutically effective amount of the crystalline salt of claim 37.

62. The method of claim 61, wherein the salt is mono hydrochloride.

63. The method of claim 61, wherein the salt is mono mesylate.

64. The method of claim 61, wherein the salt is mono sulfate.

65. A method for treating rosacea comprising administering to a subject a therapeutically effective amount of the crystalline salt of claim 37.

66. The method of claim 65, wherein the salt is mono hydrochloride.

67. The method of claim 65, wherein the salt is mono mesylate.

68. The method of claim 65, wherein the salt is mono sulfate.

69. A method for treating a gram positive bacterial infection, wherein the gram positive bacteria is selected from the group consisting of *Propionibacterium acnes, Staphylococcus aureus, Streptococcus pneumonia, Streptococcus pyogenes*, and *Clostridium difficile*, comprising administering to a subject a therapeutically effective amount of the crystalline salt of claim 37.

70. The method of claim 69, wherein the salt is mono hydrochloride.

71. The method of claim 69, wherein the salt is mono mesylate.

72. The method of claim 69, wherein the salt is mono sulfate.

* * * * *